United States Patent
Sendai et al.

(10) Patent No.: US 7,062,311 B1
(45) Date of Patent: *Jun. 13, 2006

(54) FLUORESCENCE OBSERVING APPARATUS

(75) Inventors: Tomonari Sendai, Kaisei-machi (JP);
Katsumi Hayashi, Kaisei-machi (JP);
Kazuo Hakamata, Kaisei-machi (JP);
Toshiro Hayakawa, Kaisei-machi (JP);
Yoji Okazaki, Kaisei-machi (JP); Kenji Matsumoto, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 863 days.

This patent is subject to a terminal disclaimer.

(21) Appl. No.: 09/611,229

(22) Filed: Jul. 6, 2000

(30) Foreign Application Priority Data

Jul. 7, 1999 (JP) .................................. 11-192487
Apr. 17, 2000 (JP) ............................. 2000-114702

(51) Int. Cl.
*A61B 6/00* (2006.01)

(52) U.S. Cl. ...................... 600/407; 600/160; 600/476; 356/318; 250/458.1

(58) Field of Classification Search ................ 600/407, 600/476–478, 160; 356/317, 318; 372/43–46, 372/43.01–46.016; 250/458.1, 461.2, 361 R, 250/362, 459.1, 461.1
See application file for complete search history.

(56) References Cited

U.S. PATENT DOCUMENTS

| | | | |
|---|---|---|---|
| 4,556,057 A | 12/1985 | Hiruma et al. | |
| 5,323,008 A | 6/1994 | Studholme et al. | ...... 250/458.1 |
| 5,337,328 A * | 8/1994 | Lang et al. | .................... 372/45 |
| 5,507,287 A | 4/1996 | Palcic et al. | ................. 128/633 |
| 5,647,368 A | 7/1997 | Zeng et al. | |
| 5,679,152 A | 10/1997 | Tischler et al. | ................ 117/97 |
| 5,833,617 A * | 11/1998 | Hayashi | ...................... 600/476 |
| 6,125,132 A * | 9/2000 | Okazaki | ...................... 372/75 |
| 6,232,137 B1 * | 5/2001 | Sugawara et al. | ............. 438/46 |
| 6,421,363 B1 * | 7/2002 | Osinski et al. | ................. 372/50 |
| 6,422,994 B1 * | 7/2002 | Kaneko et al. | ............. 600/160 |
| 6,433,345 B1 * | 8/2002 | Hayashi et al. | ........... 250/458.1 |
| 6,590,917 B1 * | 7/2003 | Nakayama et al. | ........... 372/45 |
| 6,900,465 B1 * | 5/2005 | Nakamura et al. | ............. 257/79 |

FOREIGN PATENT DOCUMENTS

EP 0 977 028 A1 2/2000
WO 00/13017 3/2000

* cited by examiner

*Primary Examiner*—Ruth S. Smith
(74) *Attorney, Agent, or Firm*—Sughrue Mion, PLLC

(57) ABSTRACT

A fluorescence observing apparatus including a light source for emitting excitation light, an excitation light irradiation section for irradiating the excitation light to a sample, and a fluorescence measurement section for measuring fluorescence emitted from the sample by the irradiation of the excitation light. In the fluorescence observing apparatus, a GaN semiconductor laser is employed as the light source.

27 Claims, 25 Drawing Sheets

ELS = Excitation Light Source
NOCI = Normal Observation CCD Imager

— NORMAL TISSUE
--- MORBID TISSUE

CI = CCD IMAGER

FLUORESCENCE OBSERVING APPARATUS

BACKGROUND OF THE INVENTION

1. Field of the Invention

The present invention relates to a fluorescence observing apparatus for measuring fluorescence emitted from a sample (e.g., an organism, etc.) by irradiation of excitation light to provide information which is used for diagnosis, etc., and more particularly to a fluorescence observing apparatus that employs a semiconductor laser as its excitation light source.

2. Description of the Related Art

A diagnosis instrument, etc., for acquiring the intensity and spectrum of fluorescence emitted from a sample (e.g., an organism, etc.) by irradiation of excitation light to obtain information which is used for diagnosis, are known. These diagnosis instruments employ a method of detecting fluorescence emitted when excitation light for diagnosis is irradiated to the tissue of an organism, a method of detecting fluorescence emitted by irradiating excitation light to the tissue of an organism which has beforehand absorbed a drug for fluorescence diagnosis, or similar methods. The diagnosis instrument is incorporated into an endoscope, a colposcope, an operation microscope, etc., and is utilized for observation of a fluorescence image.

For example, Japanese Unexamined Patent Publication No. 9(1997)-327433 discloses a system that uses a mercury vapor lamp as an excitation light source in order to emit self-fluorescence from the respiratory organs and the stomach and intestines. In this system, a morbid tissue is detected by detecting self-fluorescence emitted from the tissue of an organism by irradiation of the excitation light emitted from the mercury vapor lamp. It is desirable that the excitation light for emitting fluorescence from the tissue of an organism have a wavelength belonging to a short wavelength region from ultraviolet rays to visible light. Mercury vapor lamps can easily obtain high output in this wavelength region.

Also, Japanese Unexamined Patent Publication No. 59(1984)-40830 discloses an apparatus which employs an excimer dye laser as an excitation light source. In this apparatus, the excitation light emitted from this light source is irradiated to the tissue of an organism into which a photosensitive material having tumor affinity has been injected beforehand, and the fluorescence emitted from the tissue is observed. The above-mentioned technique is used for observing the tissue of an organism as a dynamic image by obtaining an image from the tissue at cycles of 1/60 sec and is capable of simultaneously observing a normal image and a fluorescence image as the dynamic image. For observation of the fluorescence image, the excitation light emitted from the excimer dye laser is irradiated to the tissue of an organism (which is a subject) with a pulse width of 30 nsec at cycles of 1/60 sec, and the fluorescence emitted from the tissue by irradiation of the excitation light is imaged by a high-sensitivity imaging device for a fluorescence image. In this way, the dynamic image is obtained. On the other hand, for observation of the normal image, white light is irradiated to the tissue of an organism (which is a subject) at cycles of 1/60 sec, while the aforementioned period of the irradiation of the excimer dye laser which is performed at cycles of 1/60 sec with a pulse width of 30 nsec is being avoided. The obtained images are formed as the dynamic image by an imaging device for a normal image.

Here, the pulsed light emission of an excimer dye laser will be output as pulsed light whose peak value is extremely high, even if the emission time is 30 nsec. Therefore, the intensity of fluorescence being emitted from the tissue subjected to the irradiation is sufficient to obtain satisfactory diagnosis information. In addition, there is almost no time lag between the irradiation of excitation light to the tissue and the emission of fluorescence from the tissue and therefore the irradiation of excitation light and the emission of fluorescence are considered nearly the same. Thus, there is no possibility that the period during which the irradiation of excitation light and the formation of a fluorescence image are performed will overlap with the period during which the irradiation of white light and the formation of a normal image are performed. Furthermore, because the formation of a fluorescence image is performed within the blanking period after the formation of a normal image which is a short time, the rate at which external light and background light (such as indoor illumination) are formed as noise components, along with the fluorescence image is extremely low.

As described above, while excimer dye lasers and mercury vapor lamps have many advantages as an excitation light source, the apparatus is extremely large in scale and extremely high in cost. Because of this, employing a small and inexpensive semiconductor laser as an excitation light source has recently been discussed.

The semiconductor laser, however, is weak in light intensity when employed as an excitation light source that is desired to emit light which has a wavelength belonging to a short wavelength region from ultraviolet rays to visible light. In addition, if the semiconductor laser is oscillated to generate a peak value greater than or equal to the continuous maximum rated output value, a phenomenon called catastrophic optical damage (COD) will arise and the end face of the active layer of the semiconductor laser will be destroyed. In this phenomenon, non-radiative recombination occurs from a defect in the end face of the active layer of the semiconductor laser, and non-radiative recombination energy is converted to heat by the thermal vibration of the lattice. Because of this heat, the temperature of the end face rises and dislocation propagates, whereby the bandgap becomes narrower. If the bandgap becomes narrower, the end face further absorbs light and generates heat, resulting in a rise in the temperature of the end face. As a result, thermal run-away occurs and finally melts the end face. Particularly, in the semiconductor laser with a large energy gap, which is employed in an excitation light source to emit light which has a wavelength belonging to a near ultraviolet region, it is difficult to inject a large current to enhance light output and also difficult to stably emit pulsed light having a peak value greater than or equal to the continuous maximum rated output value.

SUMMARY OF THE INVENTION

The present invention has been made in view of the aforementioned problems. Accordingly, the primary object of the present invention is to provide a small and inexpensive fluorescence observing apparatus that is capable of emitting high-intensity light having a wavelength belonging to a short wavelength region from ultraviolet rays to visible light (e.g., such as continuous light whose light intensity is high, pulsed light whose light intensity is high, and pulsed light whose peak value is high), as excitation light, by optimizing the material of a semiconductor laser and the setting of a method of driving the semiconductor laser.

To achieve this end, there is provided a fluorescence observing apparatus comprising a light source for emitting excitation light; excitation light irradiation means for irradiating the excitation light to a sample; and fluorescence measurement means for measuring fluorescence emitted from the sample by the irradiation of the excitation light; wherein a GaN-based semiconductor laser is employed as the light source.

In the fluorescence observing apparatus, the aforementioned excitation light emitted from the light source may be continuous excitation light and the aforementioned excitation light irradiation means may irradiate the continuous excitation light to the sample.

Also, the aforementioned excitation light emitted from the light source may be pulsed excitation light and the aforementioned excitation light irradiation means may irradiate the pulsed excitation light to the sample.

The aforementioned GaN-based semiconductor laser may be an InGaN-based semiconductor laser. In that case the active layer of the semiconductor laser may have InGaN/InGaN quantum cell structure.

In a preferred form of the present invention, the aforementioned semiconductor laser is caused to output pulsed excitation light having a peak value greater than or equal to a continuous maximum output value of the semiconductor laser by a pulse-injecting current. Also, the semiconductor laser may be driven so that an integrated value of pulse oscillation output values of the semiconductor laser per unit time becomes less than or equal to an integrated value of the continuous maximum output values of the semiconductor laser per unit time. In addition, the semiconductor laser may be provided with temperature-controlling means for controlling the semiconductor laser to a predetermined temperature and below.

The aforementioned semiconductor laser may be a broad area type or surface emission type semiconductor laser.

The aforementioned semiconductor laser may also be an array type semiconductor laser. Additionally the aforementioned semiconductor laser may be a broad area array type semiconductor laser or a surface emission array type semiconductor laser.

The aforementioned fluorescence observing apparatus may further include visible-light irradiation means for intermittently irradiating visible light to the sample, and normal image forming means for forming a normal image of the sample illuminated with the visible light; wherein the pulsed excitation light is irradiated during a non-irradiation period of the visible light.

The aforementioned irradiation of the excitation light can be performed during the time that the normal image forming means is in a vertical blanking period. Furthermore, the aforementioned pulsed excitation light can be formed from a plurality of pulses.

According to the fluorescence observing apparatus of the present invention, a GaN-based semiconductor laser is employed as a light source when measuring fluorescent emitted from a sample (e.g., an organism, etc.) by irradiating excitation light emitted from the light source, to the sample. For this reason, at a wavelength belonging to a short wavelength region from ultraviolet rays to visible light, excitation light whose intensity is high can be easily obtained and the fluorescence observing apparatus can be reduced in size and cost. The reason for this is that GaN material has a very high melting point, such as 1000° C, compared with other materials such as ZnSe (melting point 400 to 500° C) and GaAs (melting point 700° C or so) and therefore device destruction can be prevented even if non-radiative recombination takes place and that it is also very high in thermal conduction coefficient, compared with other materials such as ZnSe and GaAs and therefore the heat generated within devices is dissipated rapidly to the outside so that dislocation propagation due to a rise in the temperature of the end face can be suppressed. Furthermore, the GaN material is extremely low in dislocation mobility, compared with other materials such as ZnSe (ionic bond) and GaAs (intermediate bond between an ionic bond and a covalent bond), because it has structure like a covalent bond. As a result, even if non-radiative recombination takes place, the occurrence of thermal run-away resulting from dislocation propagation can be prevented.

Note that the aforementioned excitation light irradiation means can emit excitation light which has high output, at a high rate with less drive current, if it irradiates continuous excitation light emitted from the light source, to a sample (e.g., an organism, etc.).

Also, the aforementioned excitation light irradiation means can emit pulsed excitation light whose output is high or pulsed excitation light whose peak value is great, if it irradiates continuous excitation light emitted from the light source, to a sample (e.g., an organism, etc.). The reason for this is that GaN material has a very high melting point, such as 1000° C, compared with other materials such as ZnSe (melting point 400 to 500° C) and GaAs (melting point 700° C or so) and therefore device destruction can be prevented even if non-radiative recombination takes place and that it is also very high in thermal conduction coefficient, compared with other materials such as ZnSe and GaAs and therefore the heat generated within devices is dissipated rapidly to the outside so that dislocation propagation due to a rise in the temperature of the end face can be suppressed.

If an InGaN-based semiconductor laser is employed in place of the aforementioned GaN-based semiconductor laser, carriers are inevitably captured at a local level formed due to the composition unevenness of indium (In), etc., before they are captured at a lattice defect from which non-radiative recombination occurs. At the local level, radiative recombination is performed. Therefore, even if a defect such as dislocation is present, non-radiative recombination will not occur from the defect and the injected current can be inhibited from giving rise to generation of heat without being converted to light. As a result, even if a defect such as dislocation is present within the active layer, the occurrence of catastrophic optical damage (COD) can be prevented.

If the active layer of the aforementioned semiconductor laser has an InGaN/InGaN quantum cell structure, a quantum level is formed in the quantum cell and carriers become concentrated in the mini-band. As a result, as the efficiency of radiative recombination becomes better and the oscillating threshold current is reduced, higher light output can be obtained with less drive current.

If the aforementioned semiconductor laser is driven so that the pulse oscillation output of the semiconductor laser per unit time becomes less than or equal to the continuous maximum output of the semiconductor laser per unit time, pulsed light emission whose peak value is great can be continuously performed with stability without giving rise to thermal damage.

If the aforementioned semiconductor laser is controlled to a predetermined temperature and below, the oscillating threshold current can be reduced and the dislocation propagation due to a rise in temperature of the end face can be suppressed. As a result, as the maximum output is not limited at thermal saturation, higher output or peak power can be obtained and the lifetime can also be considerably prolonged.

If a broad area type or surface emission type semiconductor laser is employed in place of the aforementioned semiconductor laser, a high-output excitation light source can be obtained more inexpensively.

If an array type semiconductor laser is used instead of the aforementioned semiconductor laser, excitation light having an output value obtained by integrating the light outputs of laser light emitted from a plurality of places can be emitted and therefore an excitation light source with high output is obtainable more cheaply.

If the aforementioned fluorescence observing apparatus further includes the aforementioned visible light irradiation means and normal image forming means, and if pulsed excitation light is irradiated during non-irradiation period of visible light, the respective light beams can be irradiated to a sample (e.g., an organism, etc.) so that they do not interfere with each other. As a result, a fluorescence image and a normal image can be formed more accurately.

If the aforementioned irradiation of excitation light is performed during the time that the normal image forming means is in a vertical blanking period, excitation light can be irradiated to the tissue of an organism without disturbing formation of a normal image.

If the aforementioned pulsed excitation light is formed from a plurality of pulses, for example, in the case where the aforementioned pulsed excitation light is formed from a single pulse obtained by pulse drive performed by a Q-switch, etc., an output equivalent to this single pulse can be obtained as the sum of a plurality of pulse outputs and therefore the pulse peak value can be reduced. As a result, the lifetime of the semiconductor laser can be prolonged and load on a laser driver circuit is reduced, whereby a further reduction in cost and size becomes possible.

BRIEF DESCRIPTION OF THE DRAWINGS

The present invention will be described in further detail with reference to the accompanying drawings wherein.

DESCRIPTION OF THE PREFERRED EMBODIMENTS

Figure 1:
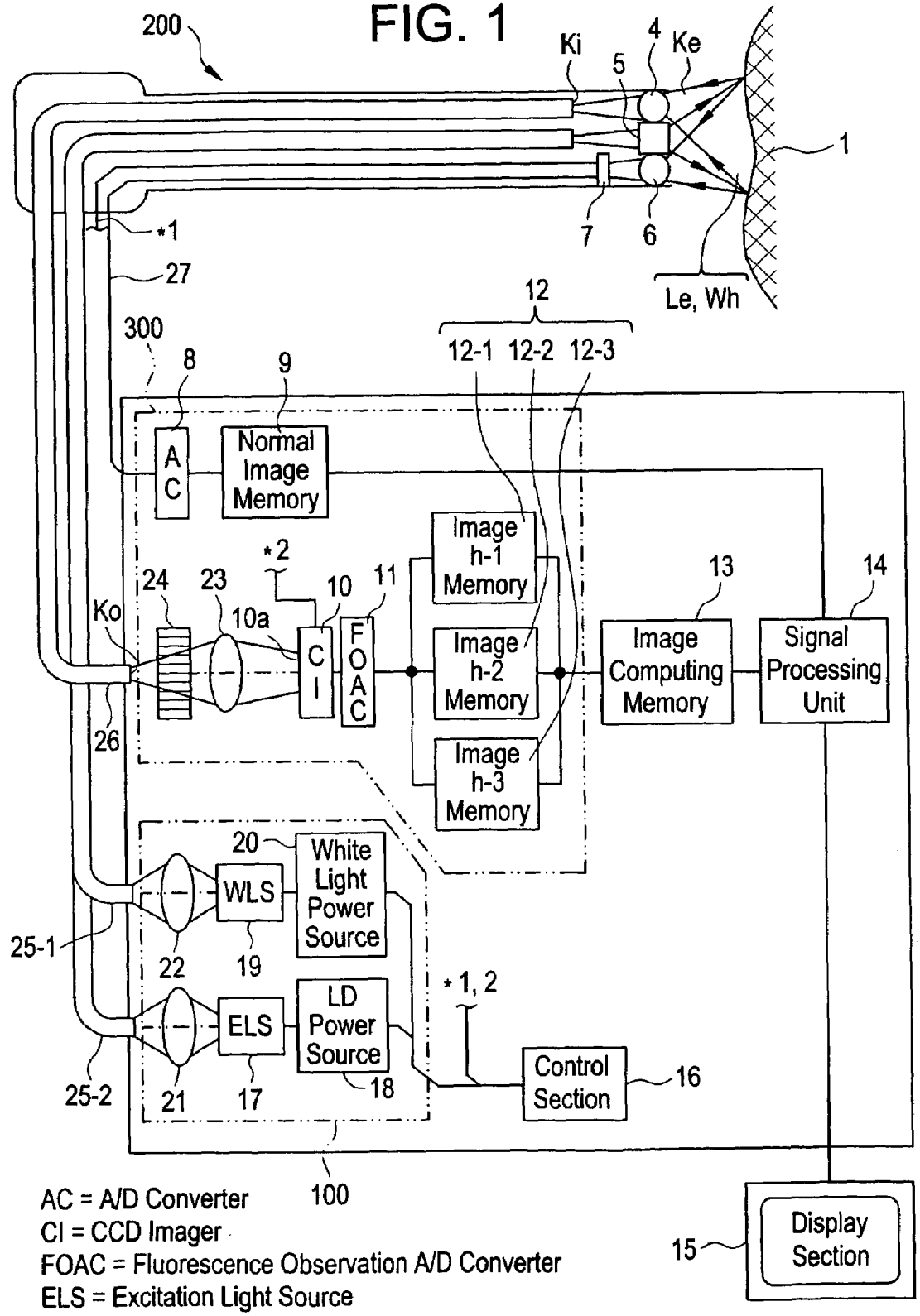
FIG. 1 is a block diagram showing a fluorescence observing apparatus constructed according to a first embodiment of the present invention.

Referring now in greater detail to the drawings and initially to FIG. 1, there is shown a fluorescence observing apparatus constructed according to a first embodiment of the present invention. The fluorescence observing apparatus comprises (1) a light source section 100 equipped with an excitation light source and a visible light (white light) source; (2) a flexible endoscope 200 for forming a normal image obtained by irradiating white light Wh guided from the light source section 100, to the tissue of an organism and also propagating the image of fluorescence (obtained by irradiating excitation light Le likewise guided from the light source section 100, to the tissue) to an optical fiber; (3) an image taking-in section 300 for taking in and storing the normal image and fluorescence image obtained by the endoscope 200, as image signals; (4) an image computing memory 13 equipped with the computation function of discriminating a cancerous tissue and a normal tissue by receiving and computing the image signals stored in the image taking-in section 300 and the storage function of storing and outputting the result of discrimination as an image signal; (5) a video signal processing circuit 14 for converting the image signal outputted from the image computation memory 13, to a video signal; (6) a display section 15 for displaying the video signal outputted by the video signal processing signal 14, as an image; and (7) a control section 16 for controlling the timings at which irradiation of the excitation light Le, irradiation of the white light Wh, reading of the normal image, reading of the fluorescence image, etc., are performed.

The white light source 19 of the light source section 100 is connected to a white-light power source 20 that is controlled by the control section 16, and the white light source 19 emits white light Wh at cycles of 1/60 sec. The white light Wh is focused by a white-light condenser lens 22 and is incident on a white-light guide 25-1. The white-light guide 25-1 is formed with a multicomponent glass fiber and connected to the light source section 100.

The excitation light source 17 of the light source section 100, on the other hand, employs an InGaN semiconductor laser of multi-quantum cell structure (active layer InGaN/InGaN). The excitation light source 17 is pulse-driven by an LD power source 18 that is controlled by the control section 16, and emits pulsed excitation light Le at cycles of 1/60 sec. The excitation light Le is focused by an excitation-light condenser lens 21 and is incident on an excitation-light guide 25-2. The excitation-light guide 25-2 is formed with a silica glass fiber and connected to the light source section 100.

Figure 2:
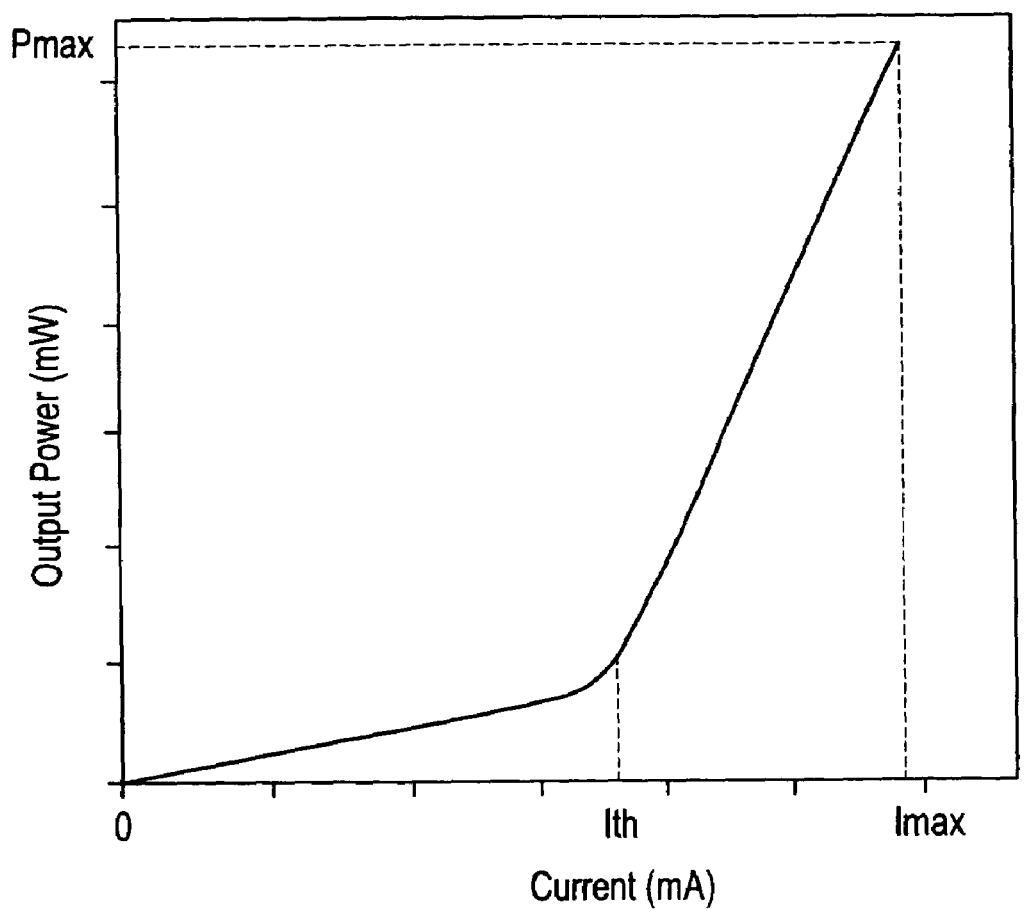
FIG. 2 is a diagram showing the power-versus-current characteristic of the semiconductor laser employed in the fluorescence observing apparatus of FIG. 1.
Figure 3:
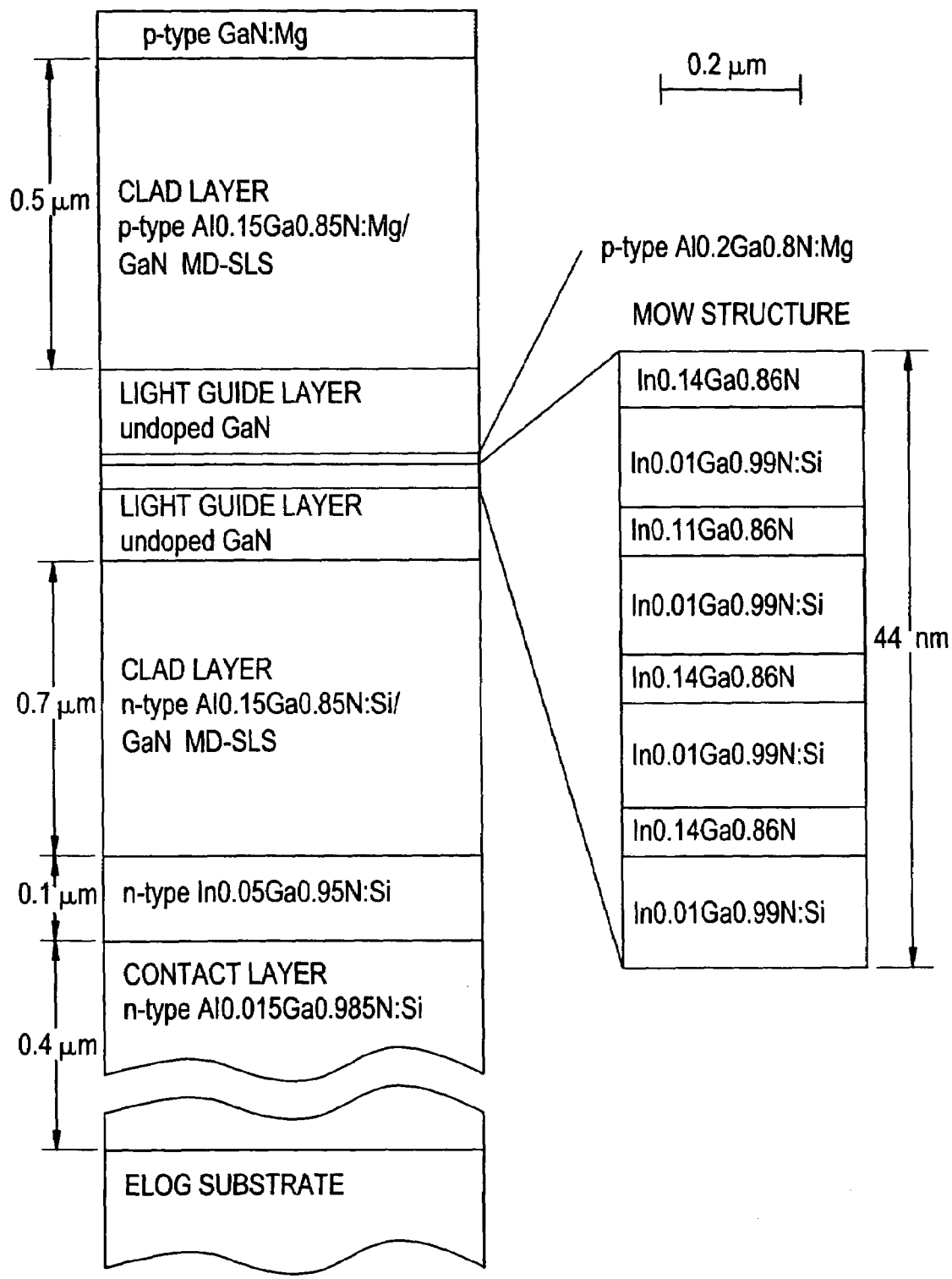
FIG. 3 is a diagram showing the internal structure of the semiconductor laser.

Note that the semiconductor laser employed in the excitation light source 17 has a continuous maximum output (continuous maximum rated output) of Pmax (mW), a continuous maximum operating current of Imax (mA), an oscillating wavelength of 410 nm (single mode), and an oscillating threshold current of Ith (mA) (Ith<Imax), as shown in FIG. 2. The structure and composition of the excitation light source 17 are shown in FIG. 3. Also, the white-light guide 25-1 and the excitation-light guide 25-2 are bundled integrally in cable form.

In the endoscope 200, the white-light guide 25-1 and the excitation-light guide 25-2 bundled integrally in cable form are inserted and disposed so that excitation light Le or white light Wh is irradiated toward a sample 1 (tissue 1) through an illuminating lens 5. The image (normal image) of the tissue 1 illuminated with white light Wh is formed on the light receiving surface of a normal-observation charge-coupled device (CCD) imager 7 through a normal-observation objective lens 6. The normal image is converted to an electrical signal by the normal-observation CCD imager 7 and transmitted to the image taking-in section 300 through a CCD cable 27. On the other hand, the image of fluorescence Ke, which occurs from the sample 1 when excitation light Le is irradiated, is formed on an end face Ki of a fluorescence image fiber 26 through a fluorescence-observation objective lens 4. The fluorescence image propagates along the fluorescence image fiber 26 and is guided to the other end face Ko of the fluorescence image fiber 26 connected to the image taking-in section 300.

For observation of a normal image, the image taking-in section 300 is provided with a normal observation A/D converter 8 for converting the electrical image signal transmitted by the CCD cable 27, to a digital image signal and a normal image memory 9 for storing the digital image signal. For observation of a fluorescence image, the image taking-in section 300 is further provided with a fluorescence observation high-sensitivity CCD imager 10 (cooling-type back irradiation CCD imager); an optical system constructed so that the fluorescence image guided to the end face Ko of the fluorescence image fiber 26 is formed on the light receiving surface of the fluorescence observation high-sensitivity CCD imager 10 by a fluorescence condenser lens 23 through an excitation-light cut filter 24 for cutting off a wavelength less than or equal to a wavelength of near 4100 nm; a fluorescence observation A/D converter 11 for converting the electrical image signal, received and converted by the fluorescence observation high-sensitivity CCD imager 10, to a digital image signal; and a fluorescence image memory 12, which consists of a fluorescence image h1 memory 12-1, a fluorescence image h2 memory 12-2, and a fluorescence image h3 memory 12-3, for storing the digital image signal.

Figure 4:
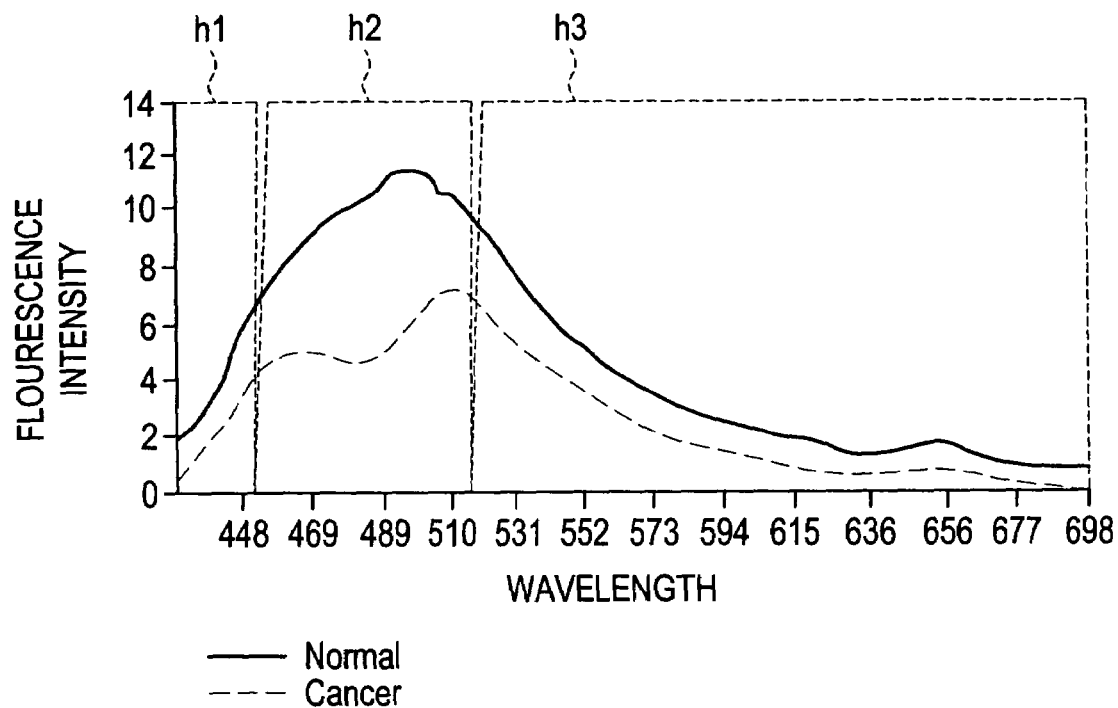
FIG. 4 is a diagram showing the wavelength regions where measurements are made and the profiles of fluorescence emitted from the tissue of an organism.
Figure 5:
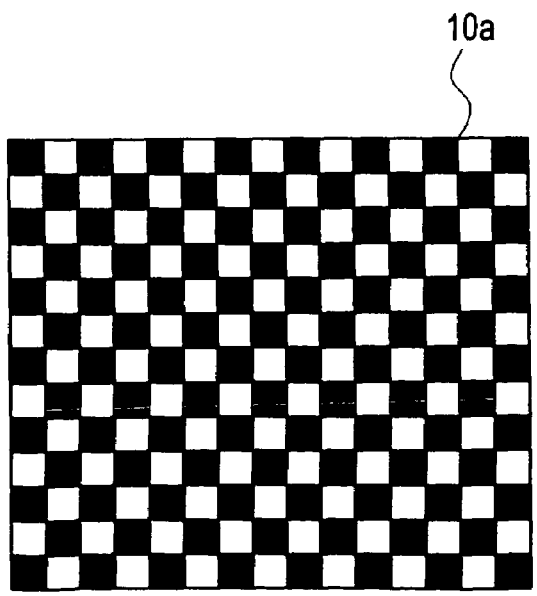
FIG. 5 is a diagram showing the structure of the mosaic filter employed in the fluorescence observing apparatus of FIG. 1.

Note that the light receiving surface of the fluorescence observation high-sensitivity CCD imager 10 has a color mosaic filter 10a such as the one shown in FIG. 5. The color mosaic filter 10a consists of sets with three kinds of filters, and the filters respectively have characteristics of transmitting only light which has a wavelength belonging to a wavelength region h1 (near 430 nm to near 445 nm), light which has a wavelength belonging to a wavelength region h2 (near 445 nm to near 520 nm), and light which has a wavelength belonging to a wavelength region h3 (near 520 nm to near 700 nm), shown in FIG. 4. The fluorescence image is separated into the wavelength bands of the 3 regions shown in FIG. 4 and is received.

Next, a description will be given of the operation in the above-mentioned first embodiment.

Figure 6:
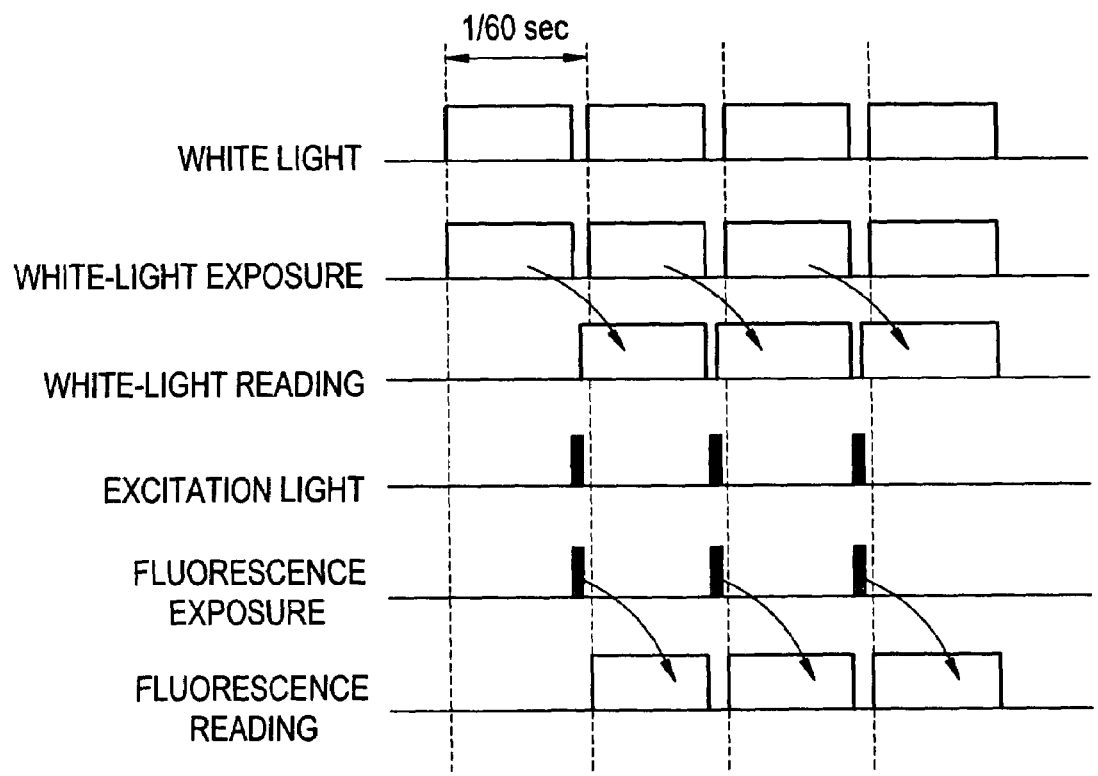
FIG. 6 is a timing chart showing the timings at which excitation light and white light are irradiated.

The fluorescence observing apparatus of the first embodiment is controlled by the controller 16 in accordance with a timing chart shown in FIG. 6. As shown in the timing chart of FIG. 6, white light Wh emitted from the white light source 19 is guided to the endoscope 200 through the white-light condenser lens 22 and the white-light guide 25-1 and illuminates the tissue 1 through the illuminating lens 5. The image of the tissue 1 illuminated with the white light Wh is formed on the light receiving surface of the normal observation CCD imager 7 by the normal-observation objective lens 6 and is exposed to the photosensitive portion of the normal-observation CCD imager 7 which consists of a plurality of photosensitive elements for converting light to electric charge. The image of the tissue 1 is converted to signal charge and accumulated. If the irradiation of the white light Wh ends, the signal charges charges accumulated in the photosensitive portion are converted to an electrical image signal by a circuit constituting the fluorescence observation high-sensitivity CCD imager 10, and the electrical image signal is read out. The electrical image signal is converted to a digital signal by the fluorescence observation A/D converter 11 and is stored in the fluorescence image h1 memory 12-1, the fluorescence image h2 memory 12-2, and the fluorescence image h3 memory 12-3.

Note that the intensity value of the fluorescence, transmitted through the filter h1 of the mosaic filter 10a, and converted to a digital value by the fluorescence observation A/D converter 11, is stored in the fluorescence image h1 memory 12-1. Also, the intensity value of the fluorescence, transmitted through the filter h2 of the mosaic filter 10a, and converted to a digital value by the fluorescence observation A/D converter 11, is stored in the fluorescence image h2 memory 12-2. Furthermore, the intensity value of the fluorescence, transmitted through the filter h3 of the mosaic filter 10a, and converted to a digital value by the fluorescence observation A/D converter 11, is stored in the fluorescence image h3 memory 12-3.

Now, the operating conditions of the InGaN semiconductor laser of multi-quantum cell structure (active layer InGaN/InGaN) employed in the excitation light source 17 will be described in detail.

This semiconductor laser is driven so that the integrated value of the oscillating output values per unit time accumulated in the photosensitive portion are converted to an electrical image signal by a circuit constituting the normal observation CCD imager 7, and the electrical image signal is read out. The electrical image signal is converted to a digital signal by the normal observation A/D converter 8 and is stored in the normal image memory 9.

If the above-mentioned irradiation of the white light Wh ends, pulsed excitation light Le emitted from the excitation light source 17 is guided to the endoscope 200 through the excitation light condenser lens 21 and the excitation light guide 25-2 and is irradiated toward the tissue 1 through the illuminating lens 5.

The fluorescence, emitted from the tissue 1 by irradiation of the excitation light Le, is formed on the end face Ki of the fluorescence image fiber 26 by the fluorescence image objective lens 4 and is propagated to the other end face Ko. With respect to the fluorescence image propagated to the end face Ko, the excitation light Le contained in the fluorescence Ke (which is a measuring object) is removed by an excitation-light cut filter 24. Then, the fluorescence image is formed on the light receiving surface of the fluorescence observation high-sensitivity CCD imager 10 having the mosaic filter 10a by the fluorescence condenser lens 23 and is exposed to the photosensitive portion of the fluorescence observation high-sensitivity CCD imager 10 and is accumulated as signal charge. If irradiation of the pulsed excitation light Le ends, the signal is less than or equal to the integrated value of the continuous maximum output values per unit time, and a pulse oscillation duty ratio is set so that a peak value greater than or equal to the continuous maximum output is obtained. When the above-mentioned semiconductor laser whose continuous maximum output is Pmax (mW) is pulse-operated at cycles of 1/60 sec, energy E equivalent to the integrated value of the oscillating output values of each pulse per unit time needs to be set to a value less than or equal to the integrated value J of the continuous maximum output values per unit time. Since the unit time is 1/60 sec, it becomes necessary to meet the conditions shown below.

Energy E of a single pulse (mJ) $\leq$ Pmax/60

Figure 7A:
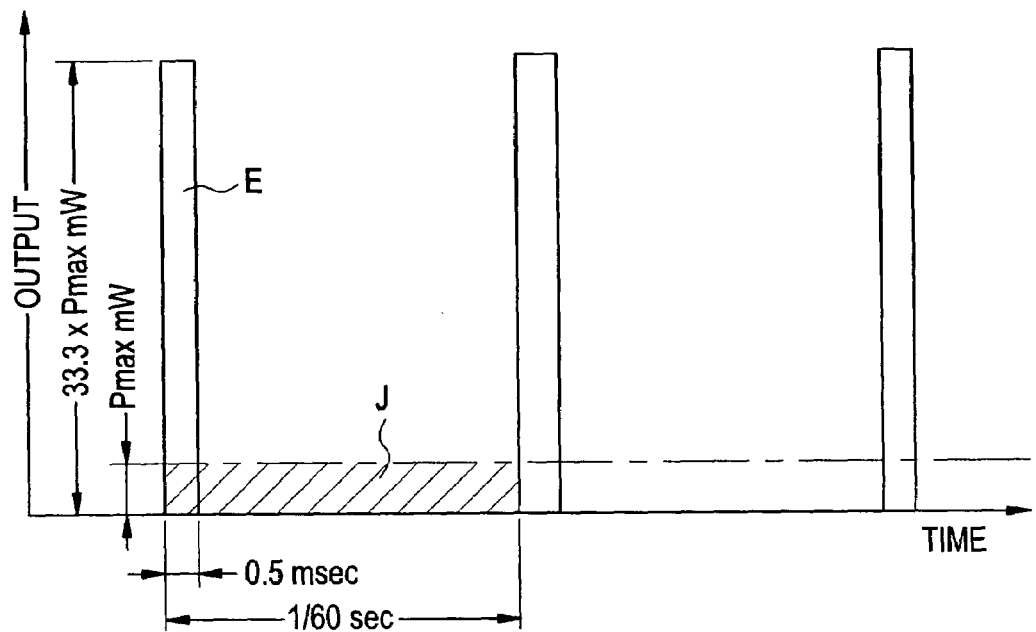
FIG. 7A is a timing diagram showing the conditions under which the semiconductor laser is driven with a pulse width of 0.5 mm.

Therefore, for example, if the pulse width of a rectangular wave generated by injection of rectangular current is made 0.5 msec, the peak value is set to the following value (see FIG. 7A).

Peak value Pp (mW) $\leq (^{1000}/_{0.5}) \times$ (Pmax/60) =Peak value Pp (mW) $\leq (^{2000}/_{60}) \times$ (Pmax/60)

Here, $(^{2000}/_{60}) \times$ (Pmax/60) $\div 33.3 \times$ Pmax

Figure 7B:
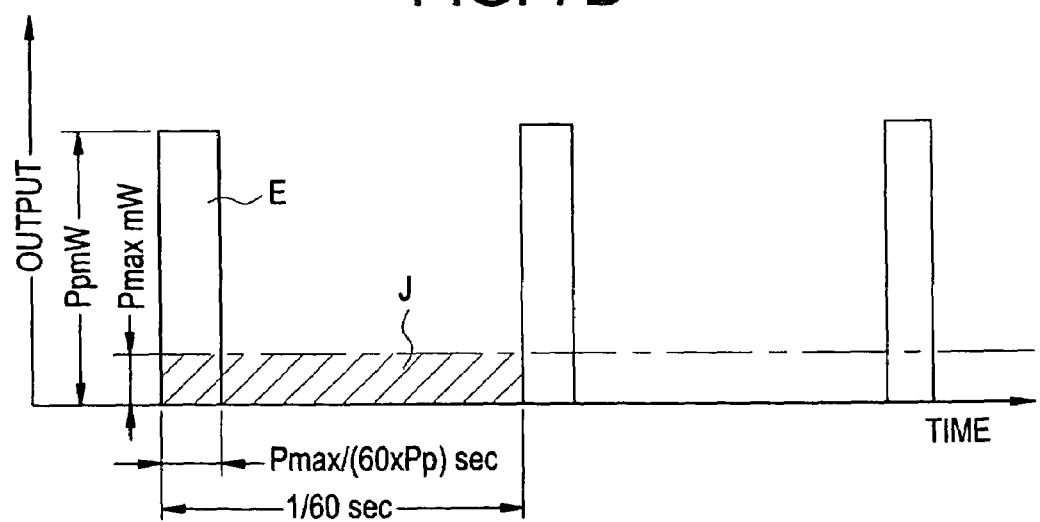
FIG. 7B is a timing diagram showing the conditions under which the semiconductor laser is driven with a peak value of 200 mm.

Also, if the peak value in the case of driving the semiconductor laser with a rectangular wave is made Pp (mW) (Pp>Pmax), the duty ratio is set so that the pulse width becomes the following value (see FIG. 7B).

Pulse width Wd (sec) $\leq$ (1/Pp) $\times$ (Pmax/60) =Pulse width Wd (sec) $\leq$ Pmax/(60$\times$Pp)

Figure 8:
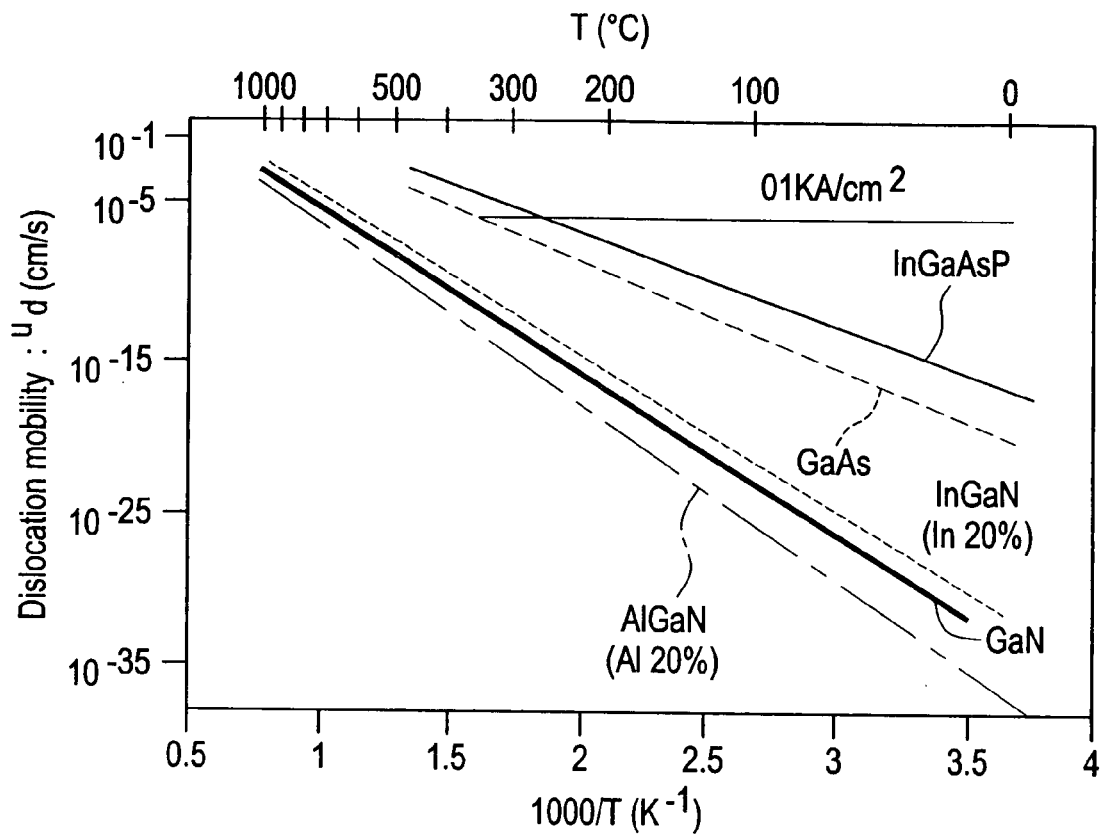
FIG. 8 is a diagram showing the temperature dependency of dislocation.

As shown in FIG. 8, InGaN is less by a factor of $10^{-10}$ in dislocation mobility at the same temperature than InGaAsP and GaAs. Also, a condition of oscillation has been alleviated because the active layer has a multi-quantum cell structure of InGaN/InGaN (i.e., luminous efficiency has been enhanced by reducing the oscillating threshold current to make temperature dependency lower). For this reason, as described above, even if the semiconductor laser is oscillated at a peak value greater than or equal to the continuous maximum output value, no catastrophic optical damage (COD) will arise and the peak value can continue high pulse oscillation with stability. In addition, the pulse drive makes the generation of heat intermittent and increases the radiating time. Therefore, because of heat generated by a crystal, doping materials, such as Mg, etc., are prevented from diffusing thermally and crossing and short-circuiting the active layer. As a result, device degradation can be prevented and device lifetime can be prolonged.

As shown in the timing chart of FIG. 6, in order to take in a normal image and a fluorescence image and obtain a dynamic image from them, it is necessary that excitation light Le and white light Wh be exposed by setting timing so that the irradiation of excitation light Le to the tissue 1 and the irradiation of white light Wh to the tissue 1 do not overlap within a period of 1/60 sec. For instance, timing needs to be set so that the irradiation of excitation light Le to the tissue 1 and the exposure of fluorescence emitted from the tissue 1 are executed during the time that the irradiation of white light Wh stops, and the time that the normal observation CCD imager 7 is in the vertical blanking period. Also, when reading out the signal charges exposed and stored in the photosensitive portion by the respective CCD imagers, the accumulated signal charges are moved and saved in a circuit other than the photosensitive portion constituting the CCD imager, and the saved signal charges are then read out. Therefore, since signal charges can be read out during a sufficient time of 1/60 sec until signal charges in the next cycle are read out, an image signal with less noise can be obtained.

The values of the image signals, stored in the fluorescence image h1 memory 12-1, the fluorescence image h2 memory 12-2, and the fluorescence image h3 memory 12-3, are output to the image computing memory 13 and given the following computing process.

Figure 9:
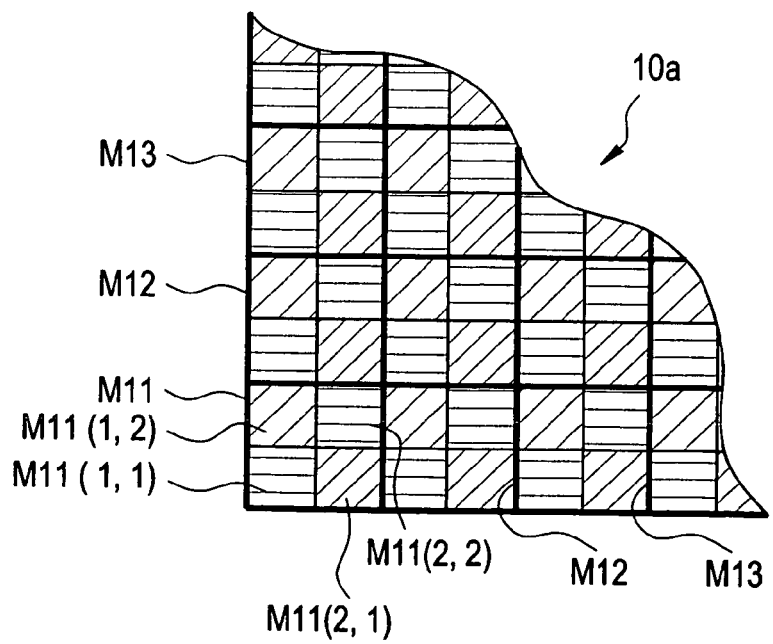
FIG. 9 is an enlarged diagram of the mosaic filter shown in FIG. 5.

As shown on an enlarged scale in FIG. 9, the mosaic filter 10a consists of a large number of matrix blocks having four microregions. For example, in the 4 microregions M11(1, 1), M11(1, 2), M11(2, 1), and M11(2, 2) within block M11, a filter h1, filters h2, and a filter h3 having a wavelength transmission characteristic such as that shown in FIG. 4 are disposed. More specifically, the filter h1, the filters h2, and the filter h3 respectively transmit only light which has a wavelength belonging to a wavelength region h1, light which has a wavelength belonging to a wavelength region h2, and light which has a wavelength belonging to a wavelength region h3. The filter h1 corresponds to the microregion M11 (1, 1), the filters h2 to the microregions M11(1, 2)

and M11 (2, 1), and the filter h3 to the microregion M11 (2, 2). Since it is generally known that, as shown in FIG. 4, at the wavelength region h2 a normal tissue is different in profile from a cancerous tissue, a discrimination between a normal tissue and a cancerous tissue becomes possible by dividing the fluorescence intensity at the wavelength h2 by the fluorescence intensity at the overall wavelength region. That is, if the intensity values of fluorescence, obtained from the individual photosensitive elements corresponding to the 4 microregions M11 (1, 1), M11 (1, 2), M11 (2, 1), and M11 (2, 2) within the block M11 of the mosaic filter 10a, are taken to be D11 (1, 1), D11 (1, 2), D11 (2, 1), and D11 (2, 2), a discrimination value DD11 for the block M11 is represented as follows:

$D11$ = fluorescence intensity transmitted through filter $h2$/fluorescence intensity at the overall wavelength region = fluorescence intensity transmitted through filter $h2$/(fluorescence intensity transmitted through filer $h1$ + fluorescence intensity transmitted through filter $h2$ + fluorescence intensity transmitted through filter $h3$)

= [{$D11$(1, 2) + $D11$(2, 1)}/2]/[$D11$(1, 1) +

{$D11$(1, 2) + $D11$(2, 1)}/2 + $D11$(2, 2)]

The discrimination value calculated in the above-mentioned manner is obtained for all the blocks of the mosaic filter 10a, that is, M11, M12, M13, M14, . . . . The discrimination value is compared with a reference discrimination value ST calculated in the same manner as the aforementioned method from a tissue judged a cancerous tissue or normal tissue, whereby a degree of difference can be obtained as a value. The result is stored in the image computing memory 13 as a differential discrimination value SS. That is, a differential discrimination value SS for block Mxy is calculated by the following equation:

SS(x, y)=DDxy−ST

The differential discrimination value SS calculated as described above is output from the image computing memory 13 and is input to the video signal processing circuit 14 along with the value of the image signal of the normal image outputted from the normal image memory 9. These signal values are processed so that the normal image and the fluorescence image are simultaneously displayed on a single screen, and are output and displayed on the display section 15 as information that is used for diagnosing a morbid part.

Figure 10:
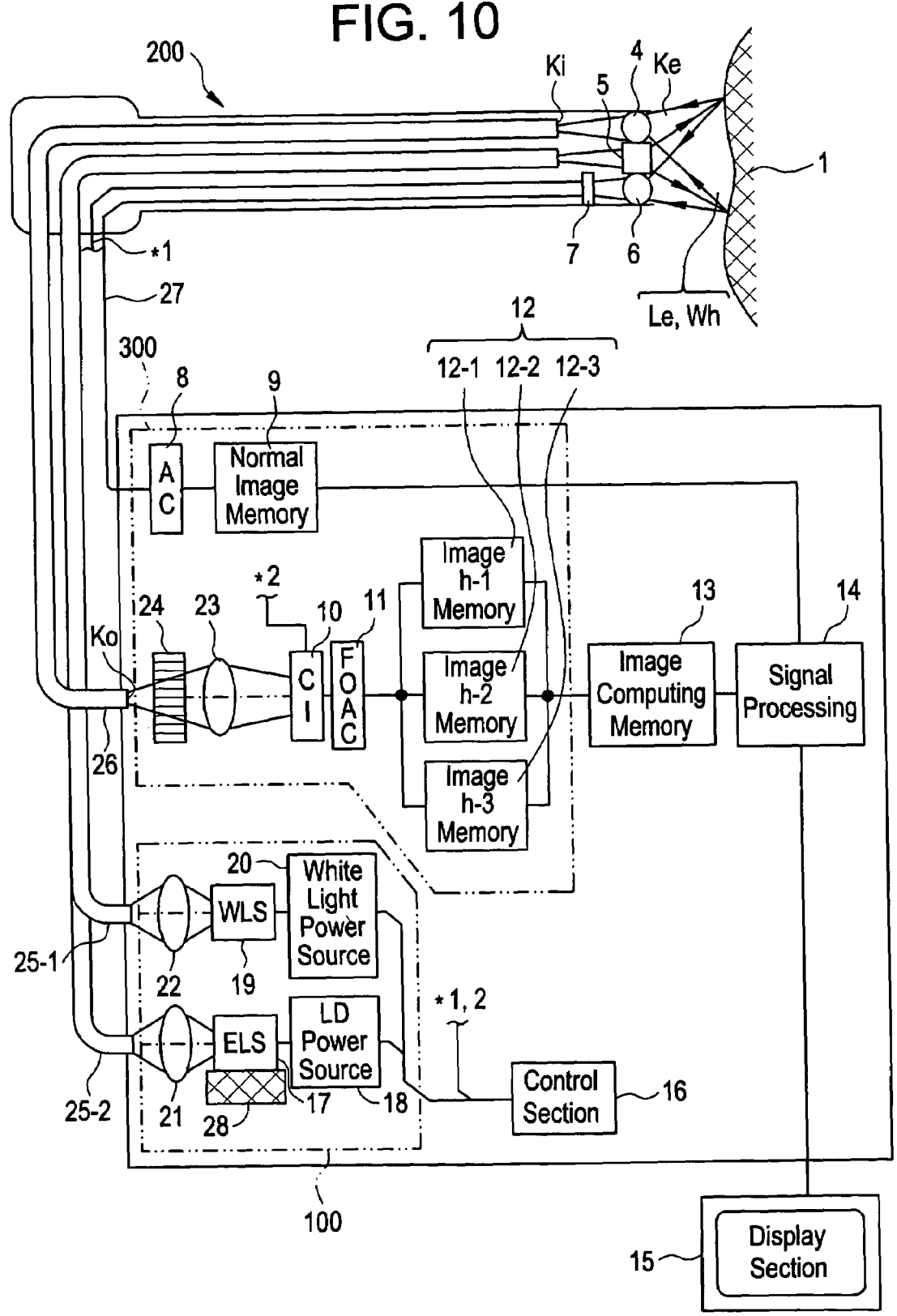
FIG. 10 is a block diagram showing the fluorescence observing apparatus including a Peltier element disposed in direct contact with the excitation light source to cool the operating temperature of the semiconductor laser.

Note that, as shown in FIG. 10, if a 1-stage Peltier element 28 is disposed in direct contact with the excitation light source 17 to cool the operating temperature of the InGaN semiconductor laser of multi-quantum cell structure (active layer InGaN/InGaN) to 10° C or less, the oscillating threshold current decreases in accordance with temperature. As a result, the lifetime of the semiconductor laser can be considerably prolonged and a higher peak value can be obtained without limiting the maximum output at thermal saturation. Furthermore, if a multi-stage Peltier element is employed to cool the above-mentioned operating down to −20° C, the above-mentioned effect can be further enhanced.

While, in the above-mentioned first embodiment, the InGaN semiconductor laser of multi-quantum cell structure (active layer InGaN/InGaN) is employed, the above-mentioned same effect which is superior to the conventional case can be obtained even in other InGaN-based semiconductor lasers and GaN-based semiconductor lasers.

Figure 11:
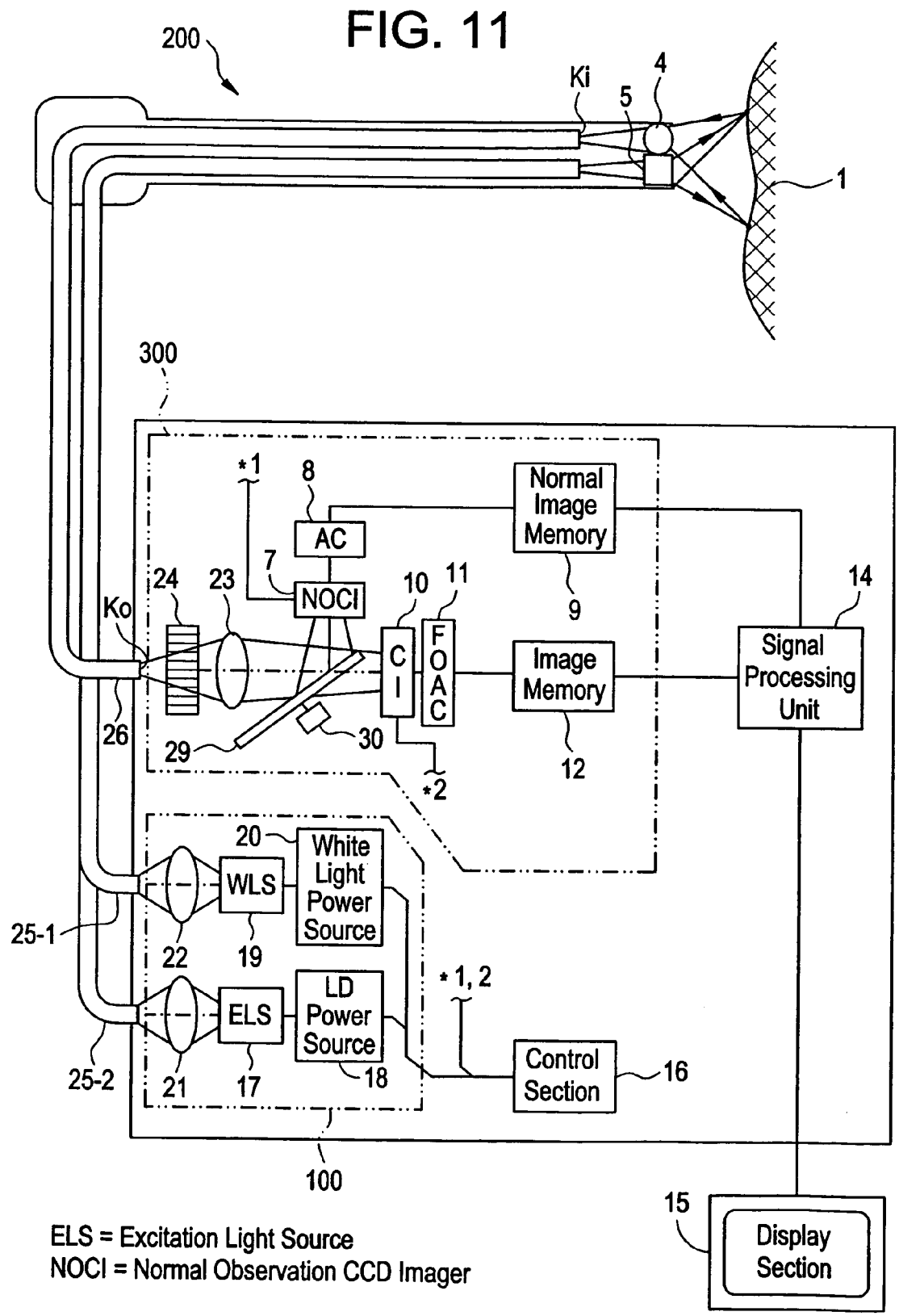
FIG. 11 is a block diagram showing a fluorescence observing apparatus constructed according to a second embodiment of the present invention.

FIG. 11 illustrates a second embodiment of the fluorescence observing apparatus constructed according to the present invention. In this second embodiment, the present invention is applied to a fluorescence endoscope for diagnosing the localization of a morbid part from a difference in the emitted state of the fluorescence emitted from a tissue absorbing photofurin II (which is a photosensitive dye) by irradiating excitation light to the tissue.

In the second embodiment, an excitation light source 17 employs an InGaN semiconductor later of multi-quantum cell structure (active layer InGaN/InGaN) of oscillating wavelength 400 nm and is pulse-operated with a dc bias current greater than or equal to an oscillating threshold current Ith (mA).

Figure 12:
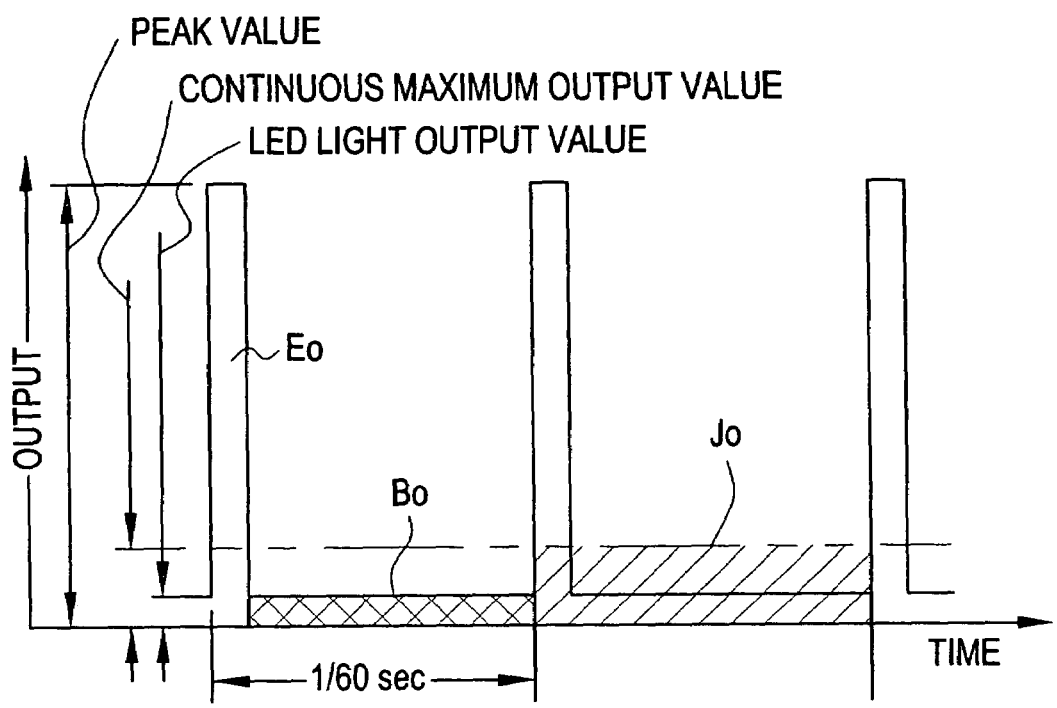
FIG. 12 is a diagram showing the relationship between the LED light output value, the continuous maximum output value, and the peak value.

In addition, the pulse oscillation of the above-mentioned semiconductor laser is driven so that, as shown in FIG. 12, the integrated value Bo of the output values per unit time (per ⅟60 sec) of LED light (spontaneous emission light), which occurs by dc bias current, and the integrated value Eo of the pulse oscillation output values per unit time become less than or equal to the integrated value Jo of the continuous maximum output values per unit time, and the pulse oscillation duty ratio is set so that a peak value greater than or equal to the continuous maximum output value is obtained. That is, the pulse oscillation duty ratio is set so that Eo+Bo≦Jo.

Furthermore, since the above-mentioned semiconductor laser is capable of oscillating a wavelength between ultraviolet and visible regions, optimum wavelength can be selected according to the excitation wavelength of a photosensitive pigment to be assumed.

In the second embodiment, an endoscope 200 has no CCD imager and therefore a normal image and a fluorescence image are both propagated to an image taking-in section 300 by an image fiber 26. The image taking-in section 300 is provided with a disc filter 29 which is rotated by a motor 30, a normal observation CCD imager 7 for forming the image of a tissue 1 illuminated with white light Wh, and a fluorescence observation high-sensitivity CCD imager 8 for forming the image of fluorescence emitted from the tissue 1 by irradiation of excitation light Le.

Figure 13:
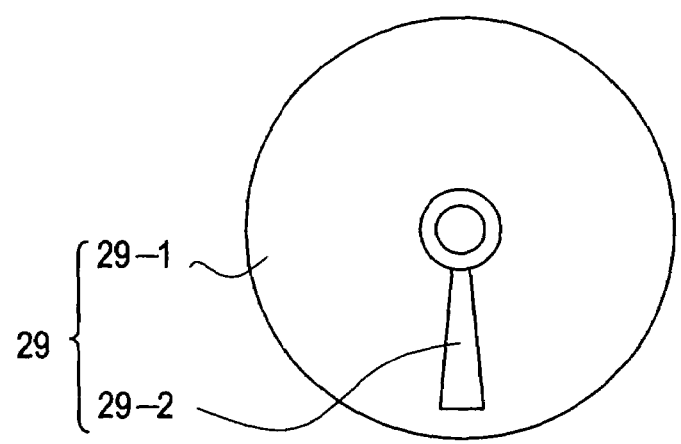
FIG. 13 is a diagram showing the structure of the disc filter employed in the second embodiment.

The filter 29 is provided with a reflection region 29-1 for reflecting light which has a wavelength belonging to a wavelength region necessary for observation of a normal image and a transmission region 29-2 for transmitting light which has a wavelength belonging to a wavelength region necessary for observation of a fluorescence image, as shown in FIG. 13. The remaining construction of the second embodiment is the same as the first embodiment.

The operation of the second embodiment of the above-mentioned construction is controlled by a controller 16 in accordance with the timing chart shown in FIG. 6, as in the first embodiment. A normal image, which is obtained when the tissue 1 is being illuminated with white light Wh, is reflected by the reflection region 29-1 of the filter 29 and formed on the light receiving surface of the normal observation CCD imager 7. On the other hand, a fluorescence image, which is obtained when excitation light Le is irradiating the tissue 1, is transmitted through the transmission region 29-2 of the filter 29 and formed on the light receiving surface of the fluorescence observation high-sensitivity CCD imager 10. The normal image formed on the light receiving surface of the normal observation CCD imager 7 is converted to signal charge and further to an image signal and is output to a normal observation A/D converter 8, in which it is converted to a digital value. The digital value is stored in a normal image memory 9. On the other hand, the fluorescence image formed on the light receiving surface of the fluorescence observation high-sensitivity CCD imager 10 is converted to signal charge and further to an image signal and is output to a fluorescence observation A/D converter 11, in which it is converted to a digital value. The digital value is stored in a fluorescence image memory 12.

The image signals, stored in the normal image memory 9 and the fluorescence image memory 12, are input to a video signal processing unit 14. The input image signals are processed so that the normal image and the fluorescence image are simultaneously displayed on a single screen, and the signals are output and displayed on the display section 15 as information that is used for diagnosing the localization of a morbid part. The remaining construction and operation of the second embodiment are the same as the first embodiment.

Figure 14:
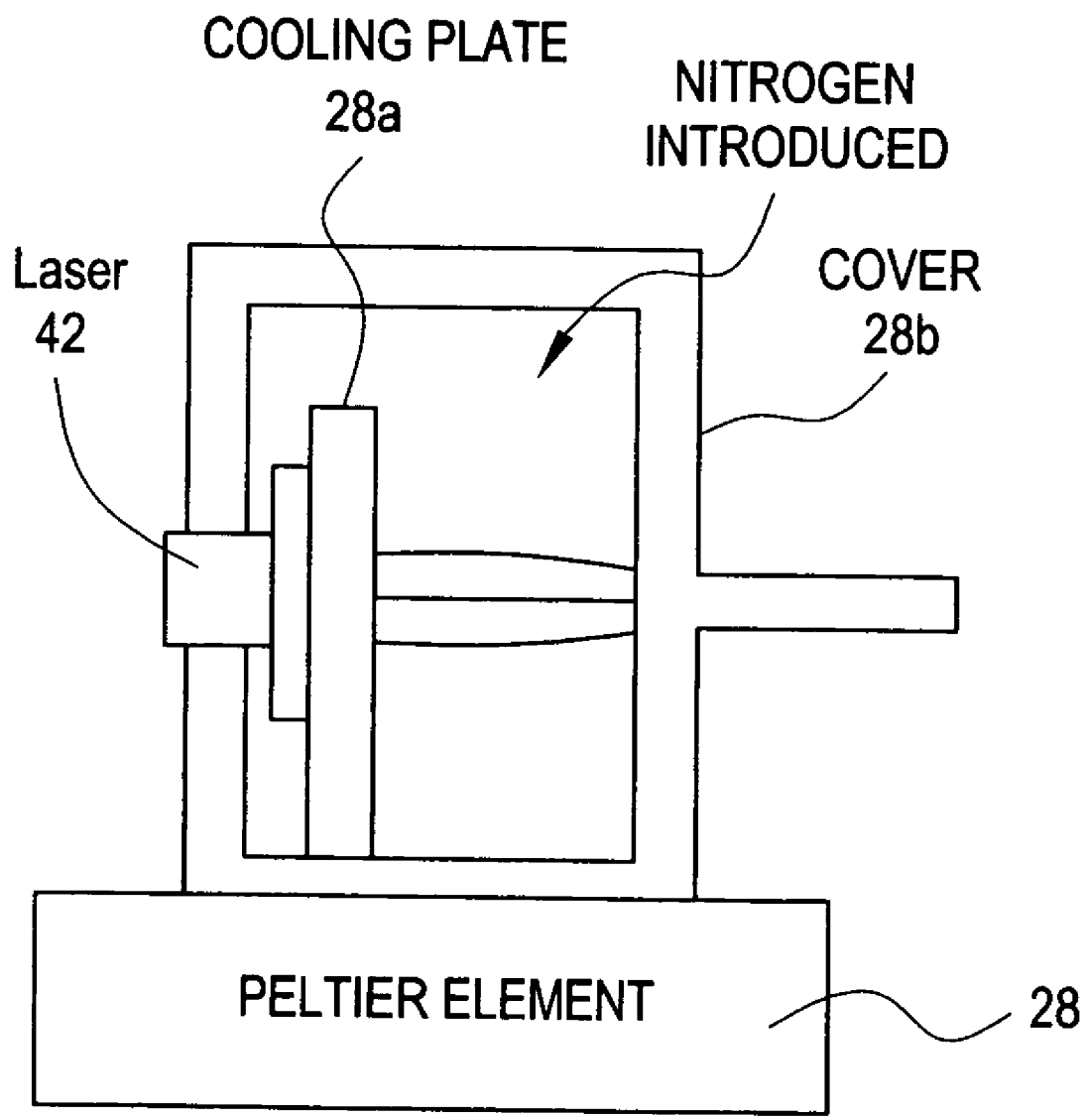
FIG. 14 is a diagram showing the temperature controlling means employed in the second embodiment.

Note that it is preferable that in order to prevent dew condensation due to cooling, the temperature controlling system (in which the Peltier element 28 described complementarily in the aforementioned first embodiment is disposed in direct contact with the excitation light source 17) be a system for fixing a semiconductor laser 42 in direct contact with a cooling plate 28a extending from the Peltier element 28, hermetically sealing the laser 42 with a cover 28b, and introducing nitrogen into the inside of the cover 28b, as shown in FIG. 14.

Figure 15:
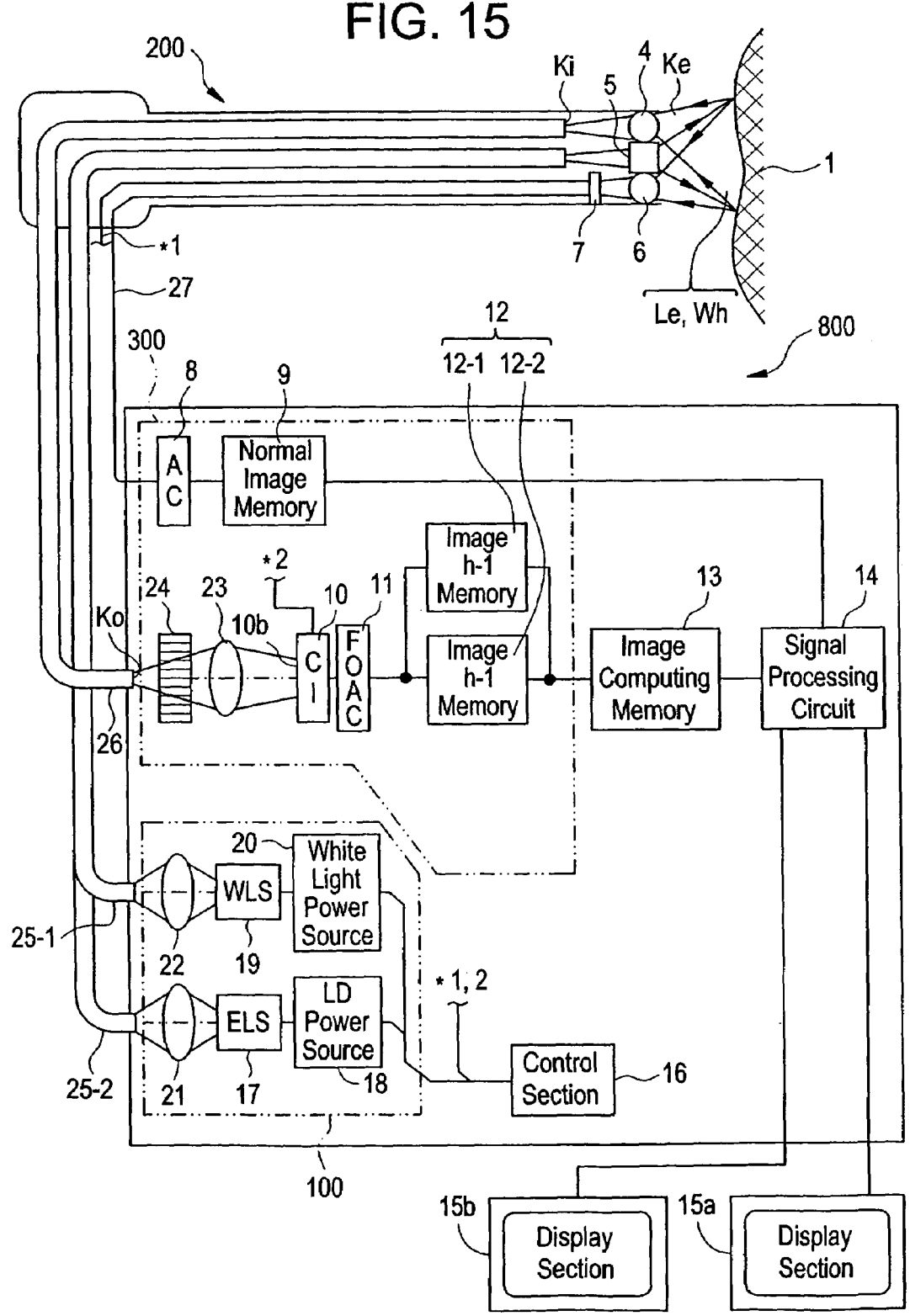
FIG. 15 is a block diagram showing a fluorescence observing apparatus constructed according to a third embodiment of the present invention.

FIG. 15 illustrates a third embodiment of the fluorescence observing apparatus constructed according to the present invention, parts with a function similar to the first embodiment being shown with the same reference numerals and characters as the first embodiment.

Figure 16:
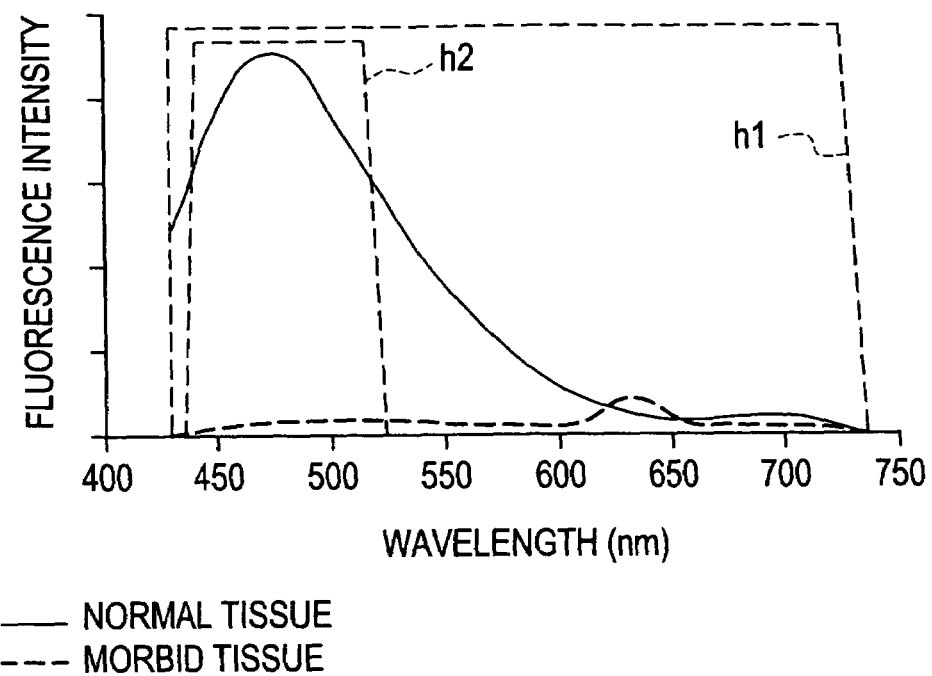
FIG. 16 is a diagram showing the intensity-versus-wavelength characteristic of the mosaic filter employed in the third embodiment.
Figure 17:
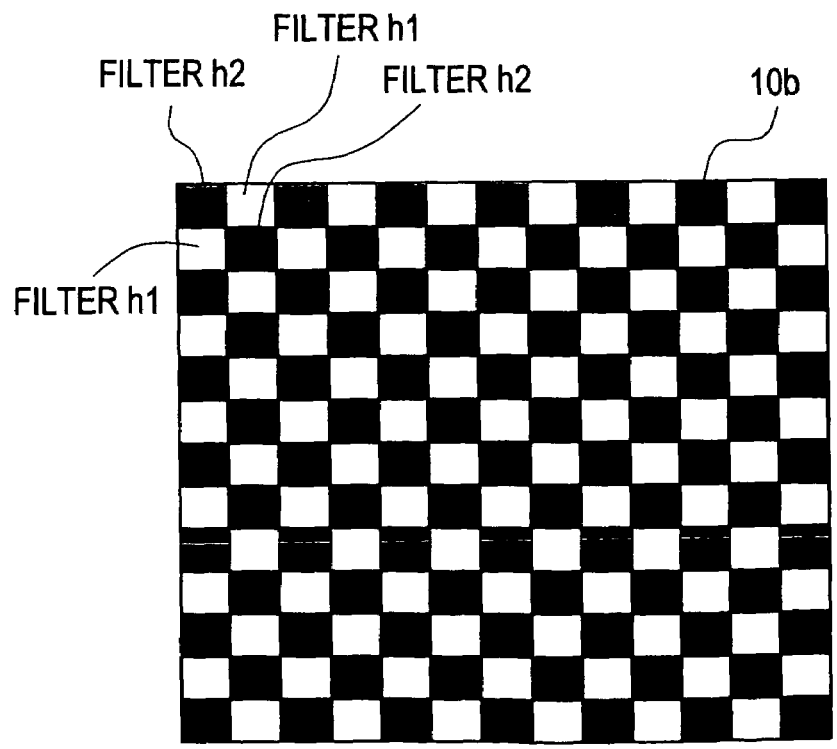
FIG. 17 is a diagram showing the structure of the mosaic filter employed in the third embodiment.

A fluorescence observing apparatus 800 in the third embodiment is the same as the first embodiment, except that the construction of a mosaic filter to be mounted on the light receiving surface of a fluorescence observation high-sensitivity CCD imager 10 is varied and the fluorescence image h3 memory 12-3 of the first embodiment is removed. The mosaic filter 10b in the third embodiment consists of a plurality of sets of two kinds, a filter h1 and a filter h2, arranged in lattice form, as shown in FIG. 17. The filter h1 and the filter h2 have a wavelength transmission characteristic such as the one shown in FIG. 16. That is, the filter h1 and the filter h2 transmit light which has a wavelength belonging to a wavelength region h1 (near 430 nm to near 740 nm) and light which has a wavelength belonging to a wavelength region h2 (near 445 nm to near 520 nm), respectively.

Next, a description will be given of the operation in the above-mentioned third embodiment.

Figure 18:
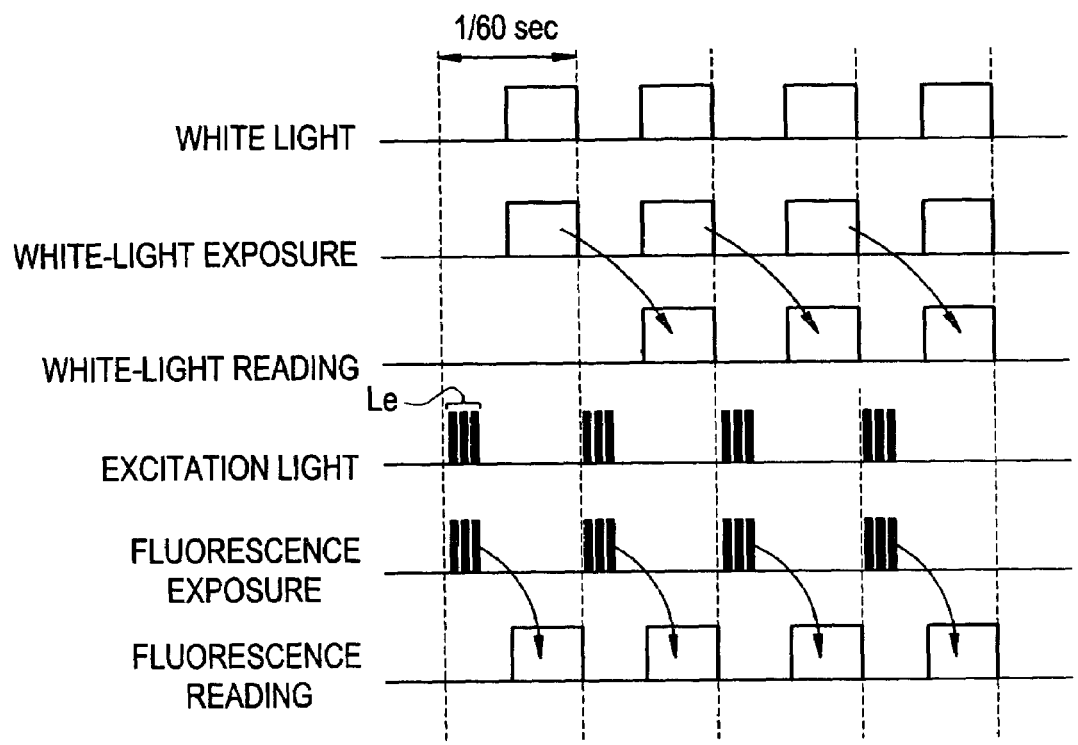
FIG. 18 is a timing chart showing the timings at which excitation light and white light are irradiated.

The fluorescence observing apparatus of the third embodiment is controlled by a controller 16 in accordance with a timing chart shown in FIG. 18. As shown in the timing chart of FIG. 18, pulsed excitation light Le, formed from 3 divided pulses having the same rectangular waveform, is emitted from an excitation light source 17. The excitation light Le is guided to an endoscope 200 through an excitation light condenser lens 21 and an excitation light guide 25-2 and is irradiated toward a tissue 1 through an illuminating lens 5.

The fluorescence, emitted from the tissue 1 by irradiation of the excitation light Le, is formed on an end face Ki of a fluorescence image fiber 26 by an fluorescence image objective lens 4 and is propagated to the other end face Ko. With respect to the fluorescence image propagated to the end face Ko, the excitation light Le contained in the fluorescence Ke (which is a measuring object) is removed by an excitation-light cut filter 24. Then, the fluorescence image is formed on the light receiving surface of a fluorescence observation high-sensitivity CCD imager 10 having the mosaic filter 10b by a fluorescence condenser lens 23 and is exposed. The fluorescence image is accumulated in the photosensitive portion of the fluorescence observation high-sensitivity CCD imager 10 as signal charge. If irradiation of the pulsed excitation light Le ends, the signal charges accumulated in the photosensitive portion are converted to an electrical image signal by a circuit constituting the fluorescence observation high-sensitivity CCD imager 10, and the electrical image signal is read out. The electrical image signal is converted to a digital value by a fluorescence observation A/D converter 11 and is stored in a fluorescence image h1 memory 12-1 and a fluorescence image h2 memory 12-2.

At this time, the intensity value of the fluorescence, transmitted through the filer h1 of the mosaic filter 10b, and converted to a digital value by the fluorescence observation A/D converter 11, is stored in the fluorescence image h1 memory 12-1. Also, the intensity value of the fluorescence, transmitted through the filter h2 of the mosaic filter 10b, and converted to a digital value by the fluorescence observation A/D converter 11, is stored in the fluorescence image h2 memory 12-2.

Here, the operating conditions of the InGaN semiconductor laser of multi-quantum cell structure (active layer InGaN/InGaN) employed in the excitation light source 17 will be described in detail.

This semiconductor laser is driven so that the integrated value of the oscillation output values per unit time is less than or equal to the integrated value of the continuous maximum output values per unit time, and the pulse oscillation duty ratio is set so that a peak value greater than or equal to the continuous maximum output value is obtained. When the above-mentioned semiconductor laser whose continuous maximum output is Pmax (mW) is pulse-operated at cycles of $\frac{1}{60}$ sec, energy E equivalent to the integrated value of the oscillation output values of the pulsed excitation light per unit time needs to be set to a value less than or equal to the integrated value J of the continuous maximum output values per unit time. Assuming the unit time is $\frac{1}{60}$ sec (time equivalent to 1 frame of a dynamic image), the continuous maximum output (maximum rated output in continuous oscillation) is Pmax=10 mW, and that the number of divided pulses in the pulsed excitation light is 3, it becomes necessary to meet the conditions shown below.

Energy E1 of each divided pulse (mJ)$\leq 10/60/3$

Figure 19:
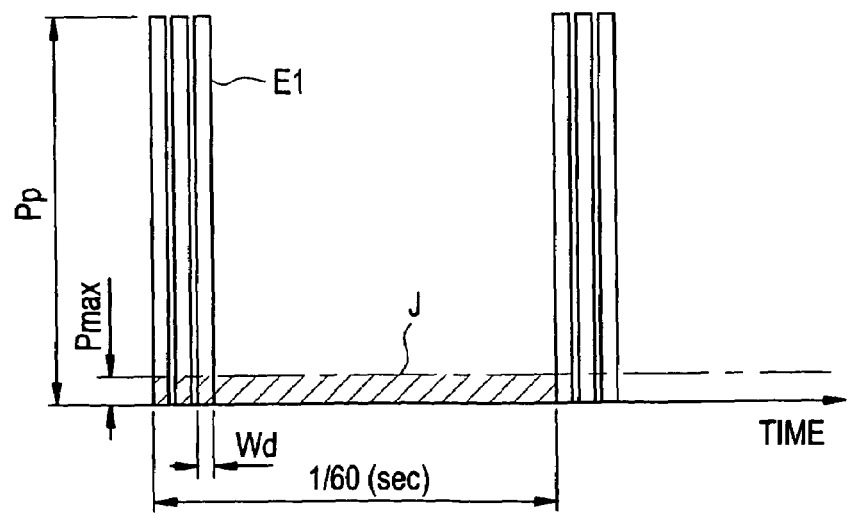
FIG. 19 is a diagram showing the relationship between the continuous maximum output value and the divided pulse peak value.

Therefore, for example, if the pulse width Wd of the divided pulse which is a rectangular wave is taken to be 0.1 μsec, the peak value Pp of the divided pulse needs to meet the following condition (see FIG. 19).

Peak value Pp (mW)$\leq$E1/Wd $=(10/60/3)\times(\frac{1}{0.1}\times 10^{-6})$
=Peak value Pp (mW)$\leq(\frac{1}{18})\times(\frac{1}{1}\times 10^{-7})$ Here, $(\frac{1}{18})\times(\frac{1}{1}\times 10^{-7})$ (unit: mW)$\div 5.6\times 10^2$ (unit: W)

When actually driving the semiconductor laser,

Peak value Pp (mW)$\leq \alpha \times 5.6\times 10^2$, because the above-mentioned value multiplied by a safe factor ($0<\alpha<1$) is set as the peak value so that the semiconductor is not destroyed.

The values of the image signals, obtained under the aforementioned setting of the pulsed excitation light, and stored in the fluorescence image h1 memory 12-1 and the fluorescence image h2 memory 12-2, are output to the image computing memory 13, in which the following computing process is performed.

Figure 20:
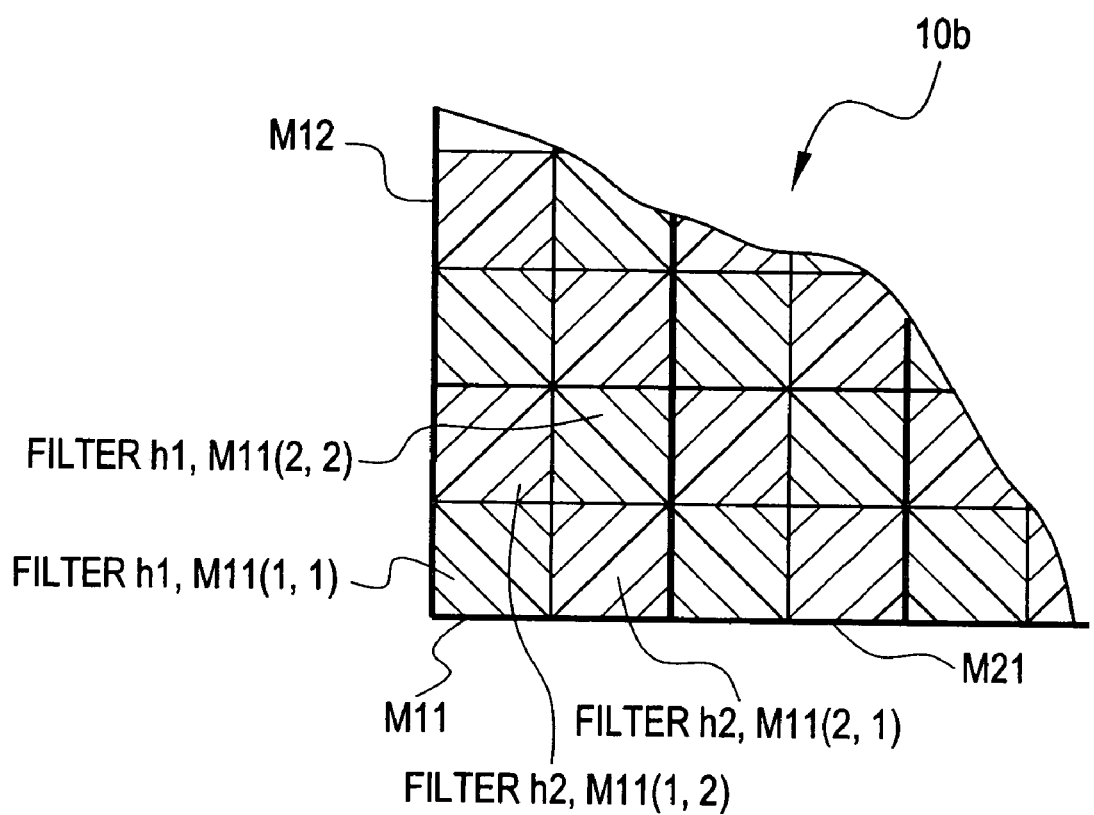
FIG. 20 is an enlarged diagram of the mosaic filter employed in the third embodiment.

As shown on an enlarged scale in FIG. 20, the mosaic filter 10b consists of a large number of matrix blocks having four microregions. For example, in the 4 microregions M11(1, 1), M11 (1, 2), M11 (2, 1), and M11 (2, 2) within block M11, filters h1 and filters h2 having the wavelength transmission character shown in FIG. 16 are disposed. The filter h1 and the filter h2 respectively transmit only light which has a wavelength belonging to a wavelength region h1 and light which has a wavelength belonging to a wavelength region h2. The filters h1 correspond to the microregions M11 (1, 1) and M11 (2, 2) and the filters h2 correspond to the microregions M11 (l, 2) and M11 (2, 1). Since it is generally known that, as shown in FIG. 16, at the wavelength regions h1 and h2 a normal tissue differs in profile from a cancerous tissue, a discrimination between a normal tissue and a cancerous tissue becomes possible by dividing the fluorescence intensity at the wavelength h2 by the fluorescence intensity at the overall wavelength region. That is, if the intensity values of fluorescence, obtained from the individual photosensitive elements corresponding to the 4 microregions M11 (1, 1), M11 (1, 2), M1 (2, 1), and M1 (2, 2) within the block M11 in the mosaic filter 10b, are taken to be D11 (1, 1), D11 (1, 2), D11 (2, 1), and D11 (2, 2), a discrimination value DD11 for the block M11 is represented as follows:

$$D11 = \text{fluorescence intensity transmitted through filters } h2/\text{fluorescence intensity at the overall wavelength region}$$

$$= \text{fluorescence intensity transmitted through filters } h2/\text{fluorescence intensity transmitted through filters } h1$$

$$= [\{D11(1, 2) + D11(2, 1)\}]/[D11(1, 1) + D11(2, 2)]$$

The discrimination value calculated in the above-mentioned manner is obtained for all the blocks of the mosaic filter 10b, that is, M11, M12, M13, M14, . . . .The discrimination value is compared with a reference discrimination value ST calculated in the same manner as the aforementioned manner from a tissue judged to be a cancerous tissue or normal tissue, whereby a degree of difference can be obtained as a value. The result is stored in the image computing memory 13 as a differential discrimination value SS.

The differential discrimination value SS calculated as described above is output from the image computing memory 13 and is input to the video signal processing circuit 14 along with the value of the image signal of the normal image outputted from the normal image memory 9. These signal values are processed so that the normal image and the fluorescence image are displayed on different display sections 15a and 15b. The remaining operation of the third embodiment is the same as the first embodiment.

While it has been described in the above-mentioned third embodiment that the pulsed excitation light, formed from 3 divided pulses having the same rectangular waveform, is irradiated to the tissue 1, the number of divided pulses is not limited to 3. The pulsed excitation light may be formed from a plurality of divided pulses. Furthermore, the pulse shape, the peak value, etc., may vary from pulse to pulse.

The irradiation of the pulsed excitation light to the tissue in the first, the second, and the third embodiment does not always need to be performed during the time that the normal observation CCD imager 7 is in a vertical blanking period. However, if the irradiation of the pulsed excitation light is performed during the time that the normal observation CCD imager 7 is in a vertical blanking period, a fluorescence image and a normal image be can obtained with higher quality within a period of 1/60 sec (1 frame).

Figure 21:
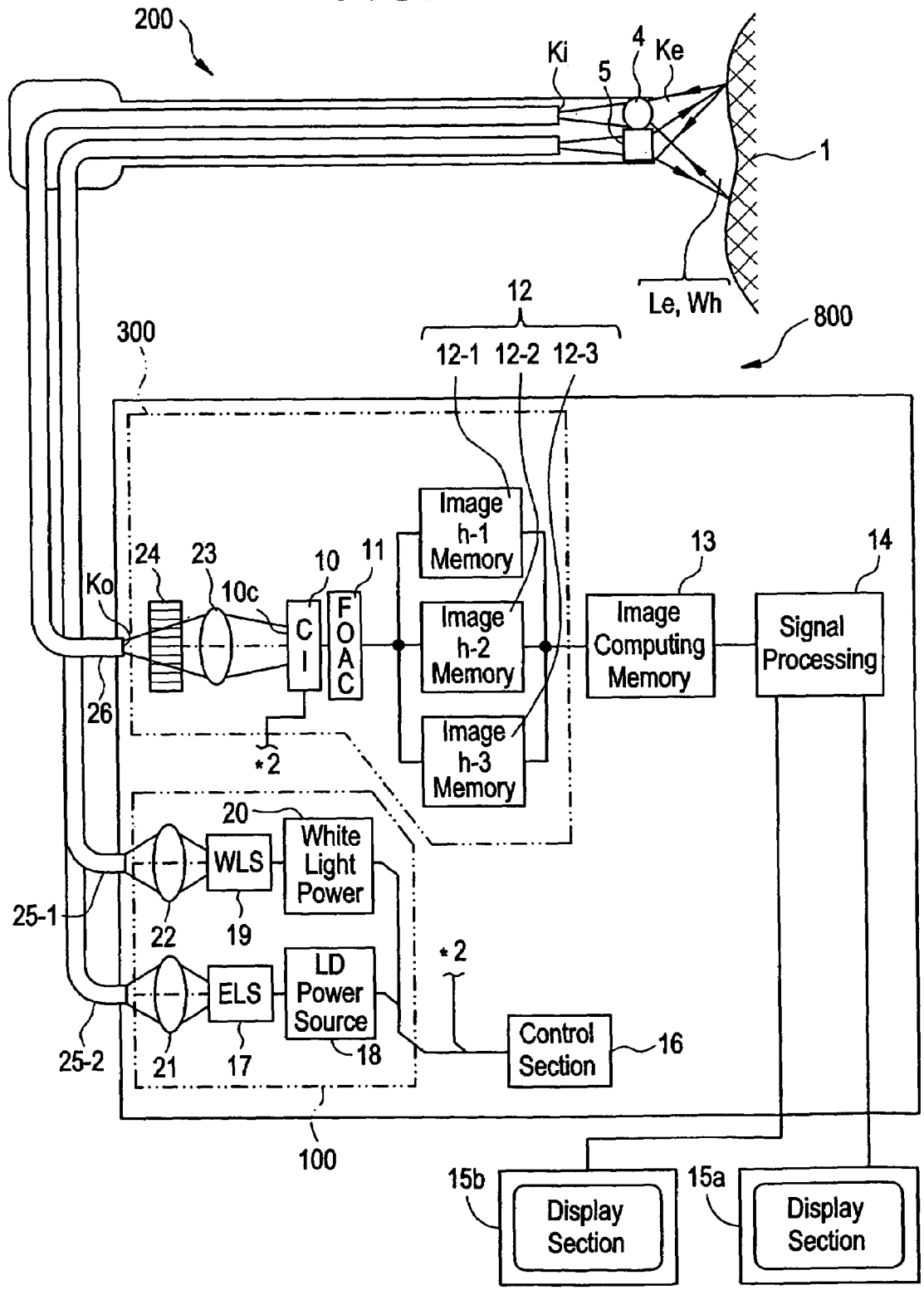
FIG. 21 is a block diagram showing a fluorescence observing apparatus constructed according to a fourth embodiment of the present invention.

FIG. 21 illustrates a fourth embodiment of the fluorescence observing apparatus constructed according to the present invention, and parts with a function similar to the first embodiment are shown with the same reference numerals and characters as the first embodiment.

In a fluorescence observing apparatus 800 of the fourth embodiment, the construction of the mosaic filter mounted on the light receiving surface of the CCD imager in the first embodiment is varied so that a normal image and a fluorescence image are both formed by a CCD imager 10. For this reason, the components for observation of a normal image, such as the normal observation objective lens 6, normal observation CCD imager 7, and CCD cable 27 of the endoscope 200 and the normal observation A/D converter 8, normal image memory 9, etc., of the image taking-in section 300, are removed. The other components are similar to the first embodiment.

Figure 22:
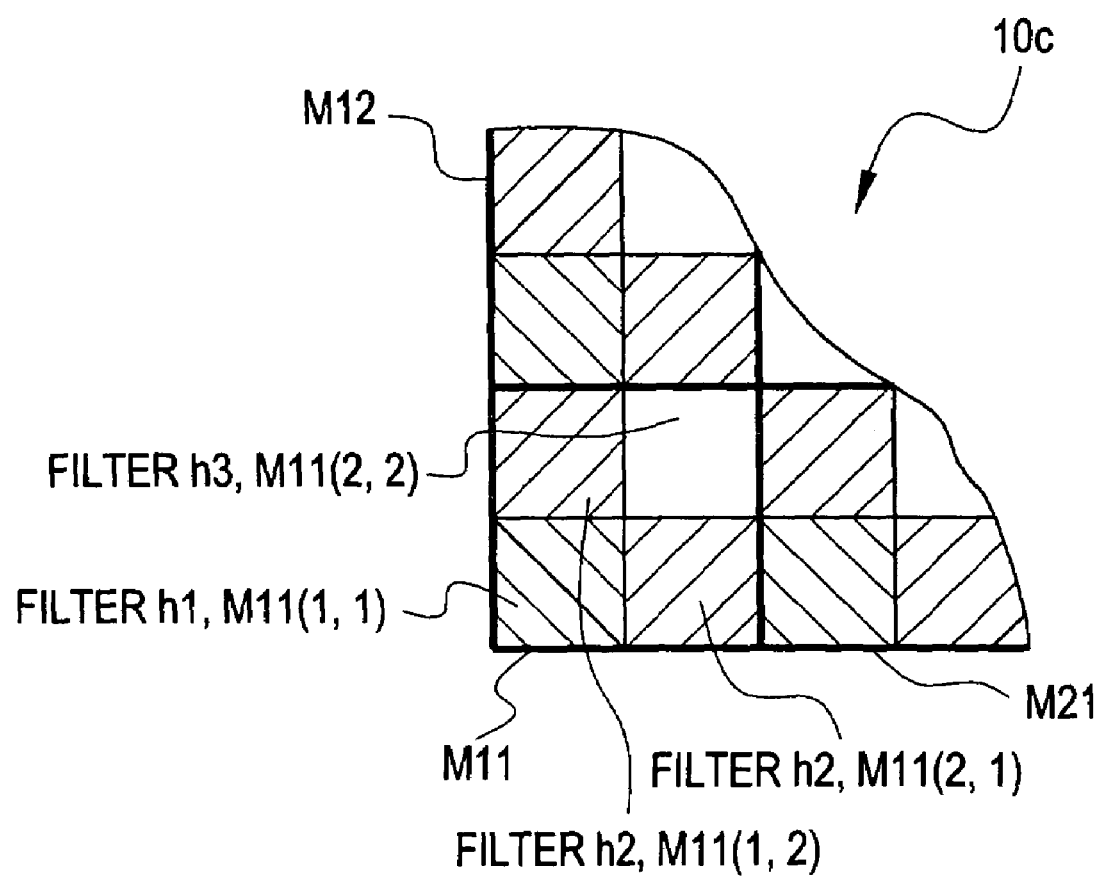
FIG. 22 is an enlarged diagram of the mosaic filter employed in the fourth embodiment.

A mosaic filter 10c in the fourth embodiment consists of a plurality of sets of a filter h1, filters h2, and a filter h3 arranged in lattice form such as that shown on an enlarged scale in FIG. 22. The filter h1 and the filter h2 have a wavelength transmission characteristic such as the one shown in FIG. 16, described in the third embodiment. That is, the filter h1 and the filter h2 transmit light which has a wavelength belonging to a wavelength region h1 (near 430 nm to near 750 nm) and light which has a wavelength belonging to a wavelength region h2 (near 445 nm to near 520 nm), respectively. The filter h3 transmits visible light (white light). In block M11, the filter h1 corresponds to the microregion M11 (1, 1), the filters h2 to the microregions M11 (1, 2) and M11 (2, 1), and the filter h3 to the microregion M11 (2, 2).

Next, a description will be given of the operation in the above-mentioned fourth embodiment.

The image signals, passed through the filter h1 and the filters h2, and formed and outputted by the CCD imager 10, are converted to digital values by the A/D converter 11. The digital values are stored in the fluorescence image h1 memory 12-1 and the fluorescence image h2 memory 12-2 and are then output to the image computing memory 13, in which the following computing process is performed.

That is, if the image signals representing the intensity values of the light received from the individual photosensitive elements of the CCD imager 10 corresponding to the 4 microregions within the block M11 in the mosaic filter 10c are taken to be D11 (1, 1), D11 (1, 2), D11 (2, 1), and D11 (2, 2), a discrimination value DD11 for the block M11 is represented as follows:

$$D11 = \text{fluorescence intensity transmitted through filters } h2/\text{fluorescence intensity at the overall wavelength region}$$

-continued

= fluorescence intensity transmitted through filters h2/(fluorescence intensity transmitted through filters $h1$

= [{$D11$(1, 2) + $D11$(2, 1)}]/[$D11$(1, 1) + {$D11$(1, 2) +

$D11$(2, 2)]

The discrimination value calculated in this manner is obtained for all the blocks of the mosaic filter 10c, that is, M11, M12, M13, M14, . . . . The discrimination value is compared with a reference discrimination value ST beforehand calculated from a tissue judged to be a cancerous tissue or normal tissue, whereby a degree of difference with the cancerous tissue or normal tissue can be calculated as a value. The result is stored in the image computing memory 13 as a differential discrimination value SS.

On the other hand, the intensity of visible light transmitted through the filter h3 is obtained as signal charge by the photosensitive element corresponding to M11 (2, 2). The signal charge is converted to a digital image signal D11 (2, 2) by the fluorescence observation A/D converter 11. The digital image signal D11 (2, 2) is stored in the fluorescence image h3 memory 12-3 and is then output and stored in the image computing memory 13.

The differential discrimination value SS, calculated in the aforementioned manner and stored in the image computing memory 13, and the value of the image signal, representing a normal image illuminated with visible light, are both input to the video signal processing circuit 14. These signal values are processed so that the normal image and the fluorescence image are displayed on different display sections 15a and 15b, respectively. The remaining operation of the fourth embodiment is similar to the first embodiment.

Figure 23:
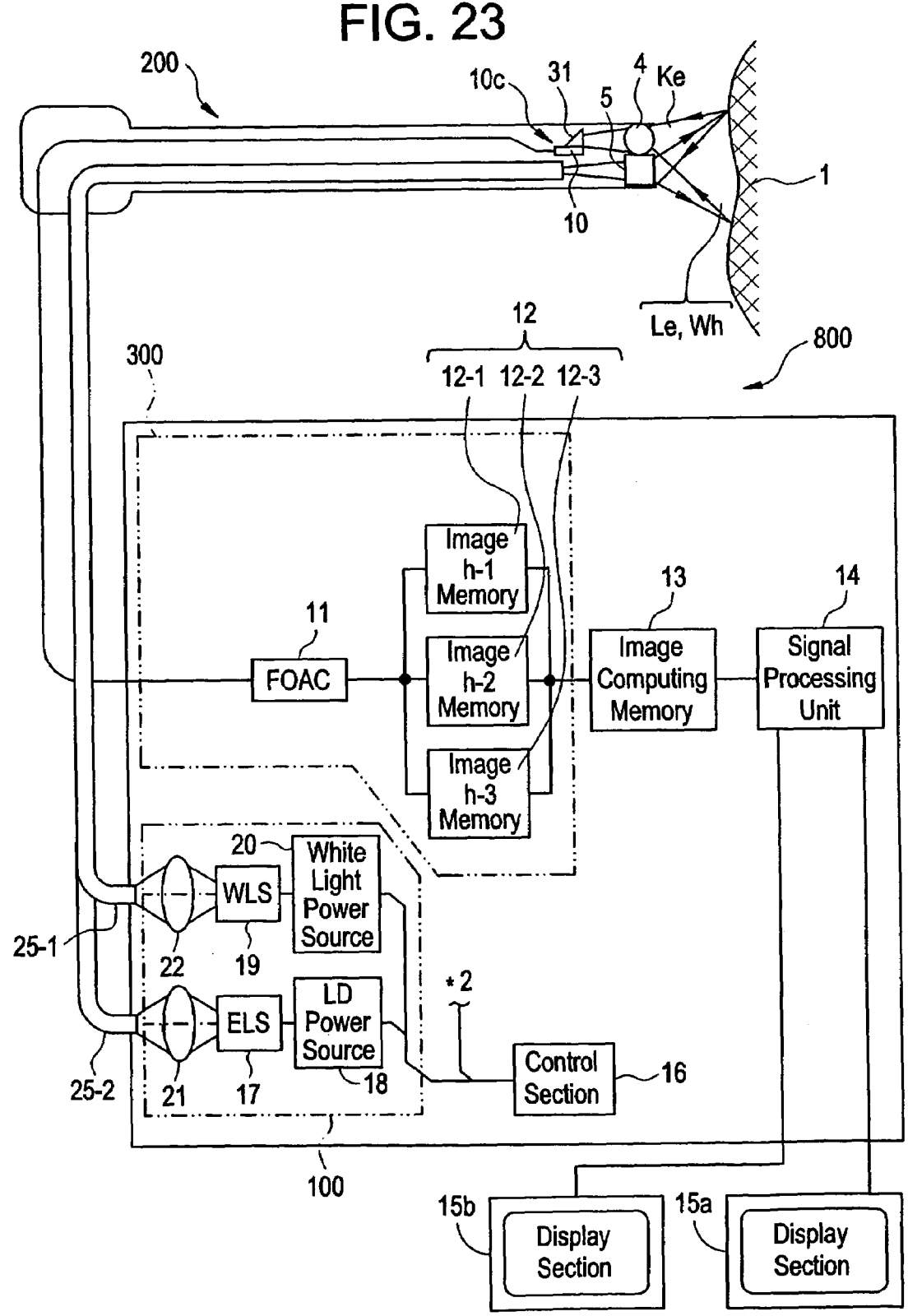
FIG. 23 is a block diagram showing the fluorescence observing apparatus including an imaging device disposed within the endoscope.

In addition, in the above-mentioned fourth embodiment, the on-chip CCD imager 10 with the mosaic filter 10c may be disposed in the endoscope 200, as shown in FIG. 23, so that a fluorescence image formed by a fluorescence image objective lens 4 can be formed directly by the CCD imager 10 without being passed through the aforementioned fluorescence image fiber 26. Note that the above-mentioned optical system for forming the image of the tissue 1, in order to easily dispose the CCD imager 10 within the endoscope 200, is constructed such that the image of the tissue 1 propagated by the fluorescence observation objective lens is changed by approximately 90 degrees in direction by a prism 31 so that it is formed on the CCD imager 10.

Figure 24:
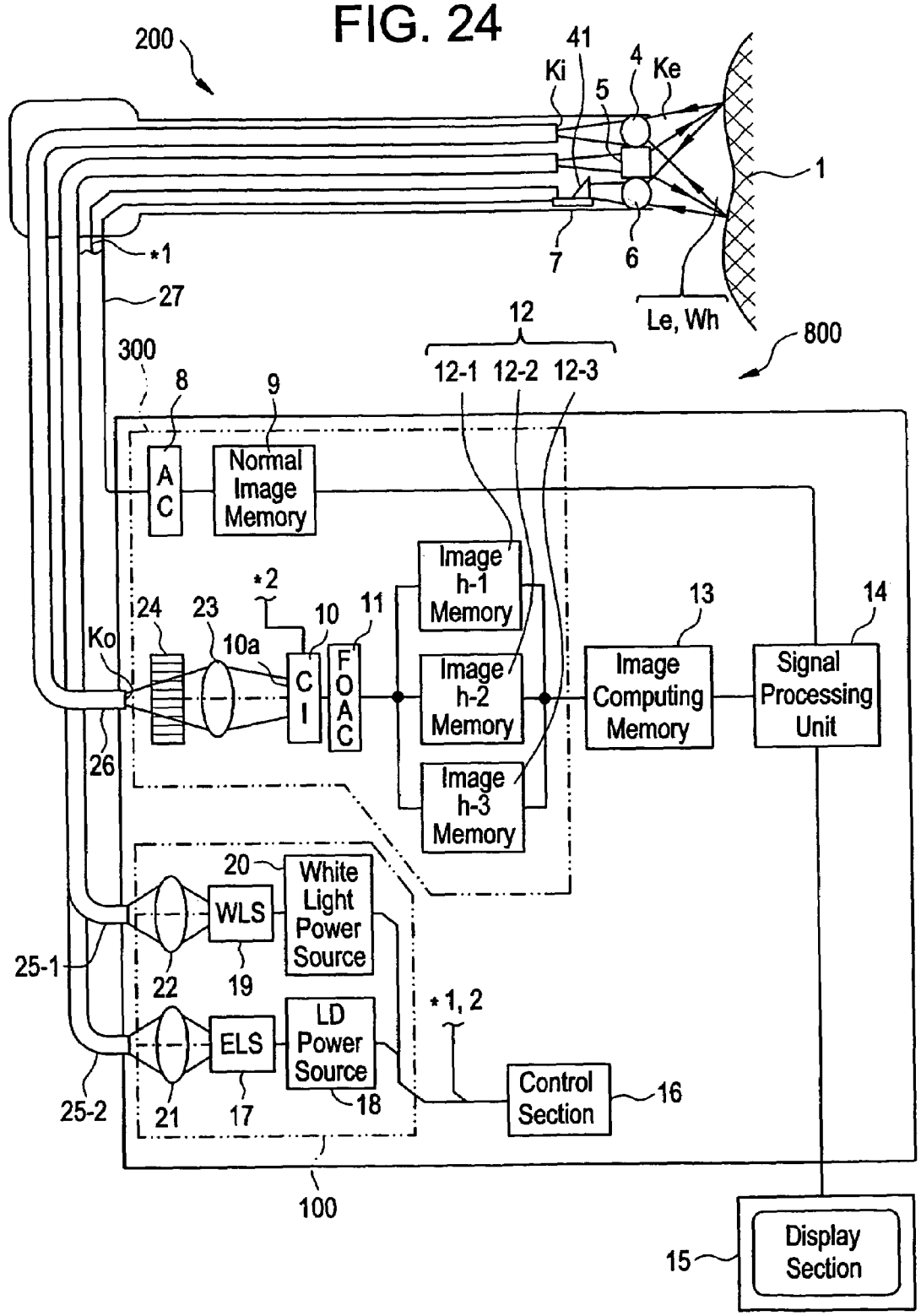
FIG. 24 is a block diagram showing a fluorescence observing apparatus constructed according to a fifth embodiment of the present invention.

FIG. 24 illustrates a fifth embodiment of the fluorescence observing apparatus constructed according to the present invention, and parts with a function similar to the first embodiment are shown with the same reference numerals and characters as the first embodiment.

A fluorescence observing apparatus 800 in the fifth embodiment includes 10 (ten) InGaN semiconductor lasers of quantum cell structure (luminescent layer InGaN/InGaN) as an excitation light source 17. In addition, the direction of an optical path for propagating the image of a tissue 1 is changed by approximately 90 degrees by a prism 41 so that the tissue image is formed on a normal observation CCD imager 7. As a result, the normal observation CCD imager 7 can be easily disposed within an endoscope 200. The remaining construction of the fifth embodiment is the same as the first embodiment.

Figure 25:
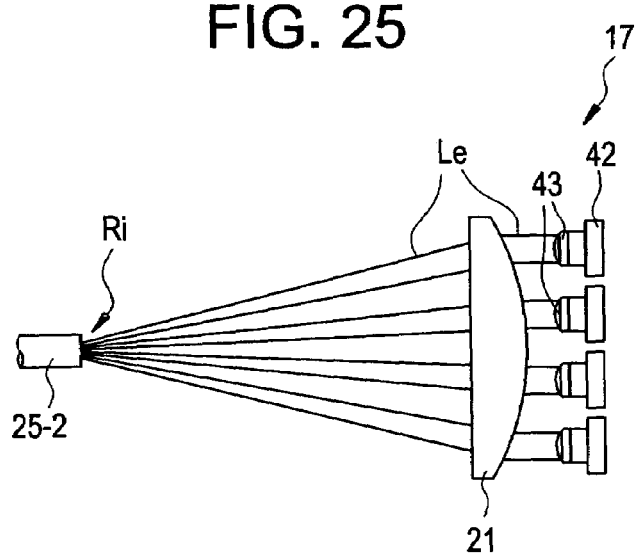
FIG. 25 is a diagram showing the structure of an excitation light source constituted of 10 semiconductor lasers.

In the excitation light source 17 constructed of 10 semiconductor lasers, as shown in FIG. 25, micro lens 43 are attached to the exit apertures of the semiconductor lasers 42 so that the excitation light Le emitted from each semiconductor laser 42 can be emitted as a collimated beam of light. Then, the collimated light beams are focused by an excitation light condenser lens 21 and incident on an end face Ri of an excitation light guide 25-2.

Next, a description will be given of the operation in the above-mentioned fifth embodiment.

While it has been described in the above-mentioned first through the fourth embodiments that the semiconductor laser is pulse-driven by the control section 16 to irradiate the pulsed excitation light Le at cycles of 1/60 sec, in the fifth embodiment the semiconductor lasers are not pulse-driven. That is, instead of performing the pulse drive of generating an output exceeding the continuous maximum output (continuous maximum rated output) by a method such as a Q-switch, pulsed excitation light is emitted by alternately producing an ON state in which the laser is being oscillated with an output within the continuous maximum output by performing continuous oscillation drive (hereinafter called CW drive) and an OFF state in which oscillation of the laser stops (or by switching on and off CW drive).

Figure 26:
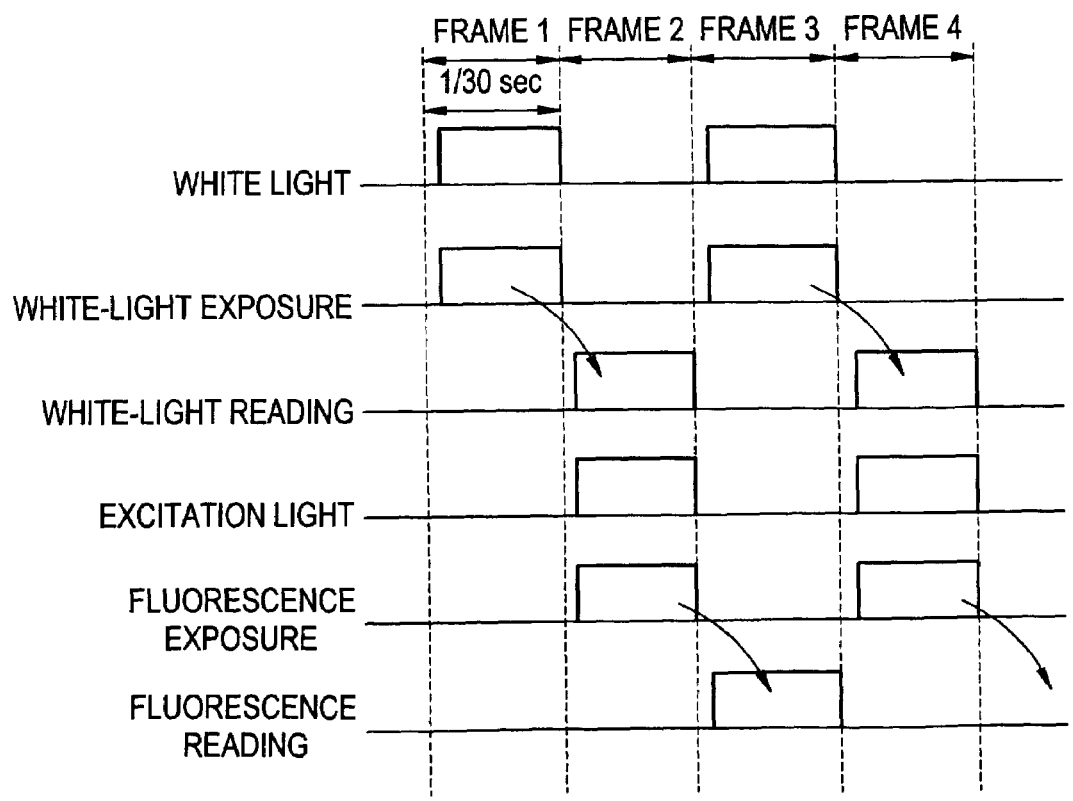
FIG. 26 is a timing chart showing the timings at which excitation light and white light are irradiated.

The fluorescence observing apparatus of the fifth embodiment is controlled by a control section 16 in accordance with a timing chart shown in FIG. 26. The white light (visible light) emitted from a white light source 19 irradiates a tissue 1 for about 1/30 sec in a period of frame 1. From a normal observation CCD imager 9 which has received the normal image illuminated with the white light, a fluorescence image received during a period of frame 2 is read out as an image signal.

On the other hand, the excitation light emitted from the excitation light source 17 by the CW drive irradiates the tissue 1 for about 1/30 sec in a period of frame 2. The fluorescence emitted from the tissue 1 by this irradiation of excitation light Le is formed on a mosaic filter 10a mounted on the light receiving surface of a fluorescence observation high-sensitivity CCD imager 10 and is exposed. The fluorescence is accumulated as signal charge in the photosensitive portion of the fluorescence observation high-sensitivity CCD imager 10. If the pulsed irradiation of the excitation light Le ends, the signal charges accumulated in the photosensitive portion are converted to an electrical image signal by a circuit constituting the fluorescence observation high-sensitivity CCD imager 10 within a period of frame 3, and the electrical image signal is read out.

Thus, a fluorescence image and a normal image can be obtained as a dynamic image of 1 frame/ (1/15) sec by alternately irradiating the white light Wh and the excitation light Le at cycles of a period of about 1/30 sec. The remaining operation in the fifth embodiment is the same as the first embodiment.

Figure 27:
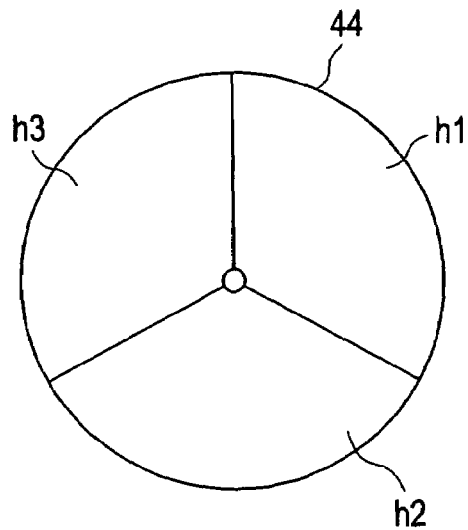
FIG. 27 is a plan view showing the rotating filter employed in the fifth embodiment, the rotating filter consisting of three 120-degree fan filters.
Figure 28:
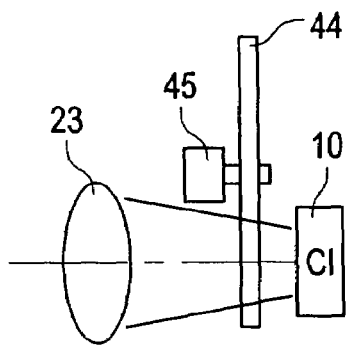
FIG. 28 is a diagram showing the position where the rotating filter is disposed.

In addition, instead of using the mosaic filter 10a mounted on the light receiving surface of the fluorescence observation high-sensitivity CCD imager 10, a rotating filter 44 such as that shown in FIG. 27 may be used. The rotating filter 44 has 120-degree fan filters h1, h2, and h3 equipped with the same wavelength transmission characteristic as the mosaic filter 10a, and therefore, the fan filters h1, h2, and h3 respectively transmit light which has a wavelength belonging to a wavelength region h1 (near 430 nm to near 445 nm), light which has a wavelength belonging to a wavelength region h2 (near 445 nm to near 520 nm), and light which has a wavelength belonging to a wavelength h3 (near 520 nm to near 750 nm). As shown in FIG. 28, the rotating filter 44 is mounted on the rotating shaft of a motor 45 and interposed between the fluorescence observation high-sensitivity CCD imager 10 and the fluorescence observation condenser lens 23. The rotating filter 44 is rotated so that it makes one revolution in $\frac{1}{30}$ sec. In this way, the fluorescence, which is incident on the light receiving surface of the fluorescence observation high-sensitivity CCD imager 10 during periods of even frames such as frame 2, frame 4, etc., in the timing chart of FIG. 26, can be separated into its spectral components and imaged in a time-divided manner.

Figure 29:
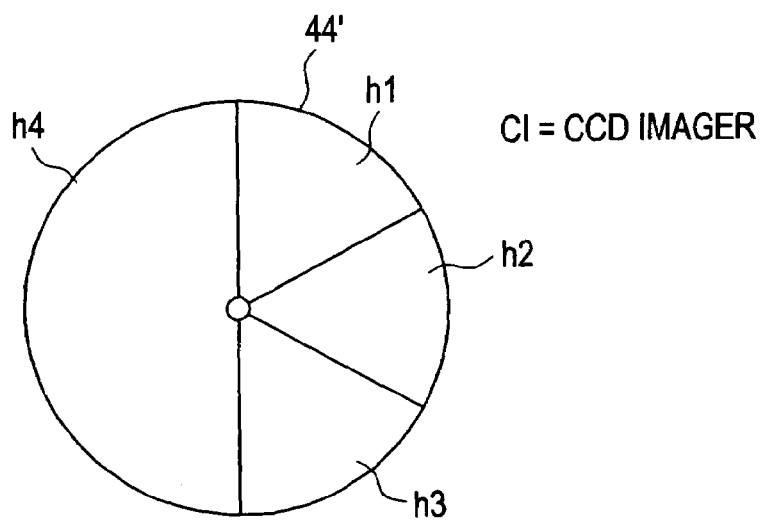
FIG. 29 is a plan view showing the construction of a rotating filter consisting of 4 filters.

Furthermore, in place of the rotating filter 44, a rotating filter 44' such as the one shown in FIG. 29 may be employed. The rotating filter 44' has 60-degree fan filters h1, h2, and h3 equipped with the same wavelength transmission characteristic as the aforementioned filter and further has a semicircular filter h4. The rotating filter 44' is mounted on the rotating shaft of the motor 45 and interposed between the fluorescence observation high-sensitivity CCD imager 10 and the fluorescence observation condenser lens 23. The rotating filter 44 is rotated so that it makes one revolution in $\frac{1}{15}$ sec. In this way, the fluorescence, which is incident on the light receiving surface of the fluorescence observation high-sensitivity CCD imager 10 during periods of even frames such as frame 2, frame 4, etc., in the timing chart of FIG. 26, can be separated into its spectral components and imaged in a time-divided manner by the filters h1, h2, and h3, and during odd frames such as frame 1, frame 3, etc., the filter h4 can transmit the wavelength region of visible light and form a normal image. Note that in the above-mentioned case, the components for forming a normal image, such as the normal observation objective lens 6, the normal observation CCD imager 7, etc., become unnecessary. The image signal, which represents the normal image formed and outputted by the fluorescence observation high-sensitivity CCD imager 10 through the filter h4 in the rotating filter 44', is input to the normal observation A/D converter 8 and is output to the video signal processing circuit 14 via the normal image memory 9.

Figure 30:
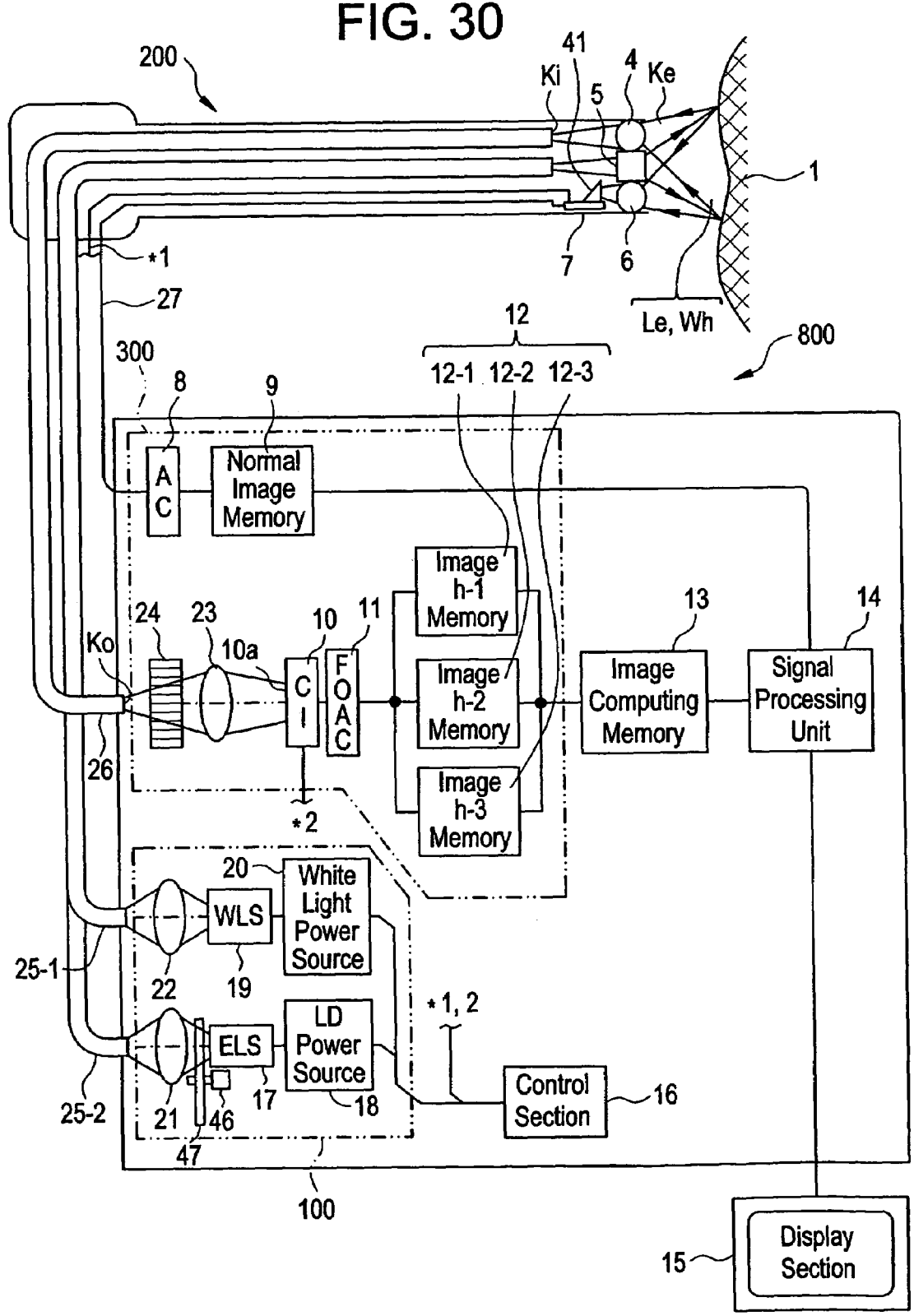
FIG. 30 is a block diagram showing a fluorescence observing apparatus constructed according to a sixth embodiment of the present invention.

FIG. 30 illustrates a sixth embodiment of the fluorescence observing apparatus constructed according to the present invention, parts with a function similar to the fifth embodiment being shown with the same reference numerals and characters as the fifth embodiment.

The fluorescence observing apparatus 100 in the sixth embodiment is the same as the fifth embodiment, except that a rotating light-source filter 47 mounted on the rotating shaft of a motor 46 is interposed between an excitation light condenser lens 21 and an excitation light source 17.

Figure 31:
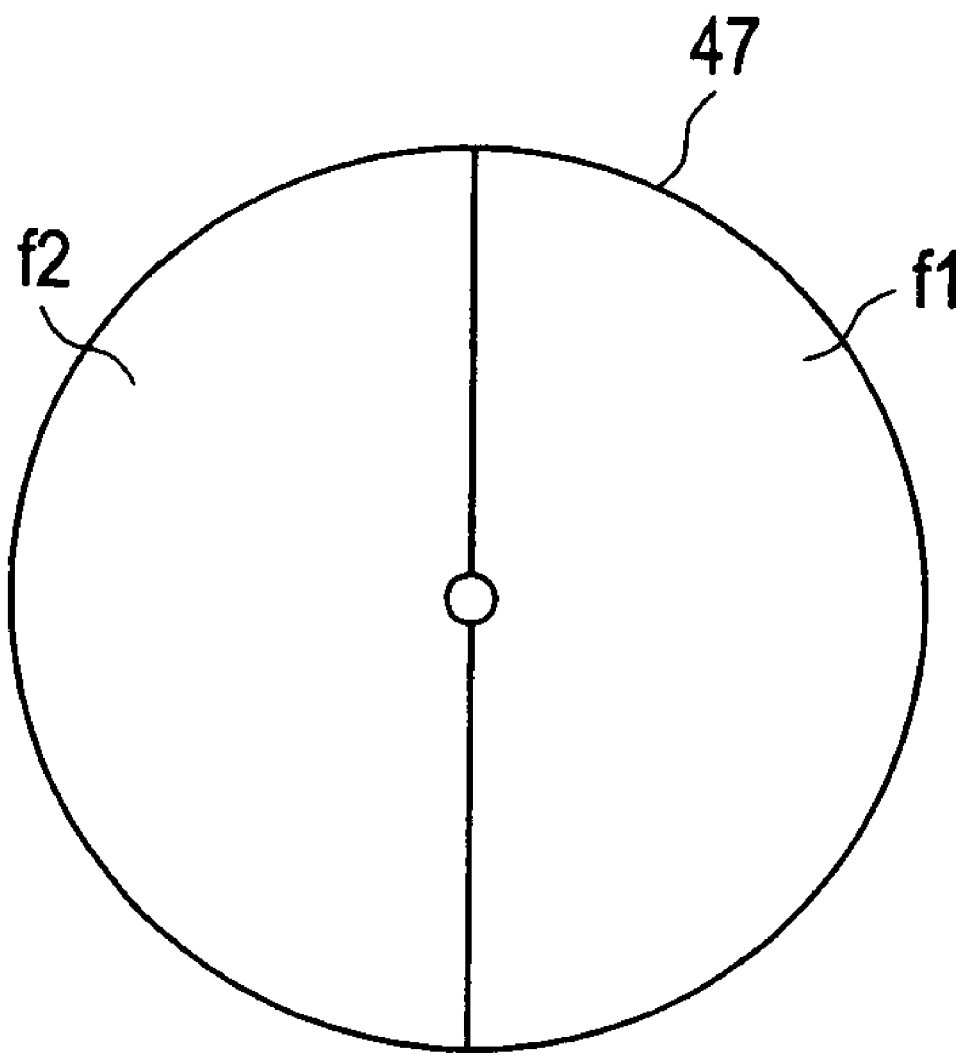
FIG. 31 is a plan view showing the construction of the rotating light source filter employed in the sixth embodiment.

Note that the rotating light-source filter 47, as shown in FIG. 31, has a semicircular filter f1 for transmitting light of near 430 nm to near 750 nm and a semicircular filter f2 for intercepting light. The rotating light-source filter 47 is rotated by a motor 46 so that it makes one revolution in $\frac{1}{15}$ sec.

Next, a description will be given of the above-mentioned sixth embodiment.

While it has been described in the above-mentioned fifth embodiment that the pulsed excitation light is emitted by alternately producing an ON state in which the laser is being oscillated with an output within the continuous maximum output by performing CW drive of the excitation light source 17 consisting of 10 InGaN semiconductor lasers and an OFF state in which oscillation of the laser stops (or by switching on and off CW drive), in the sixth embodiment the CW drive of 10 InGaN semiconductor lasers is always performed. That is, the pulsed excitation light is emitted, by switching on the CW drive at all times without switching the CW drive on or off and by rotating the rotating light-source filter 47 so that it makes one revolution in $\frac{1}{15}$ sec.

The white light source 19 and the excitation light source 17 of the light source section 100 are controlled by a control section 100 in accordance with the timing chart shown in FIG. 26, as in the aforementioned embodiments. The whitelight emitted from the white light source 19 irradiates a tissue 1 for about $\frac{1}{30}$ sec of each of the odd frames including a period of frame 1. On the other hand, the excitation light being emitted from the excitation light 17 by performing CW drive at all times irradiates the tissue 1 for about $\frac{1}{30}$ sec of each of the even frames including a period of frame 2.

Thus, a fluorescence image and a normal image can be obtained as a dynamic image of 1 frame/($\frac{1}{15}$) sec by alternately irradiating the white light wh and the excitation light Le at cycles of a period of about $\frac{1}{30}$ sec. The remaining operation in the sixth embodiment is the same as the fifth embodiment.

Figure 32:
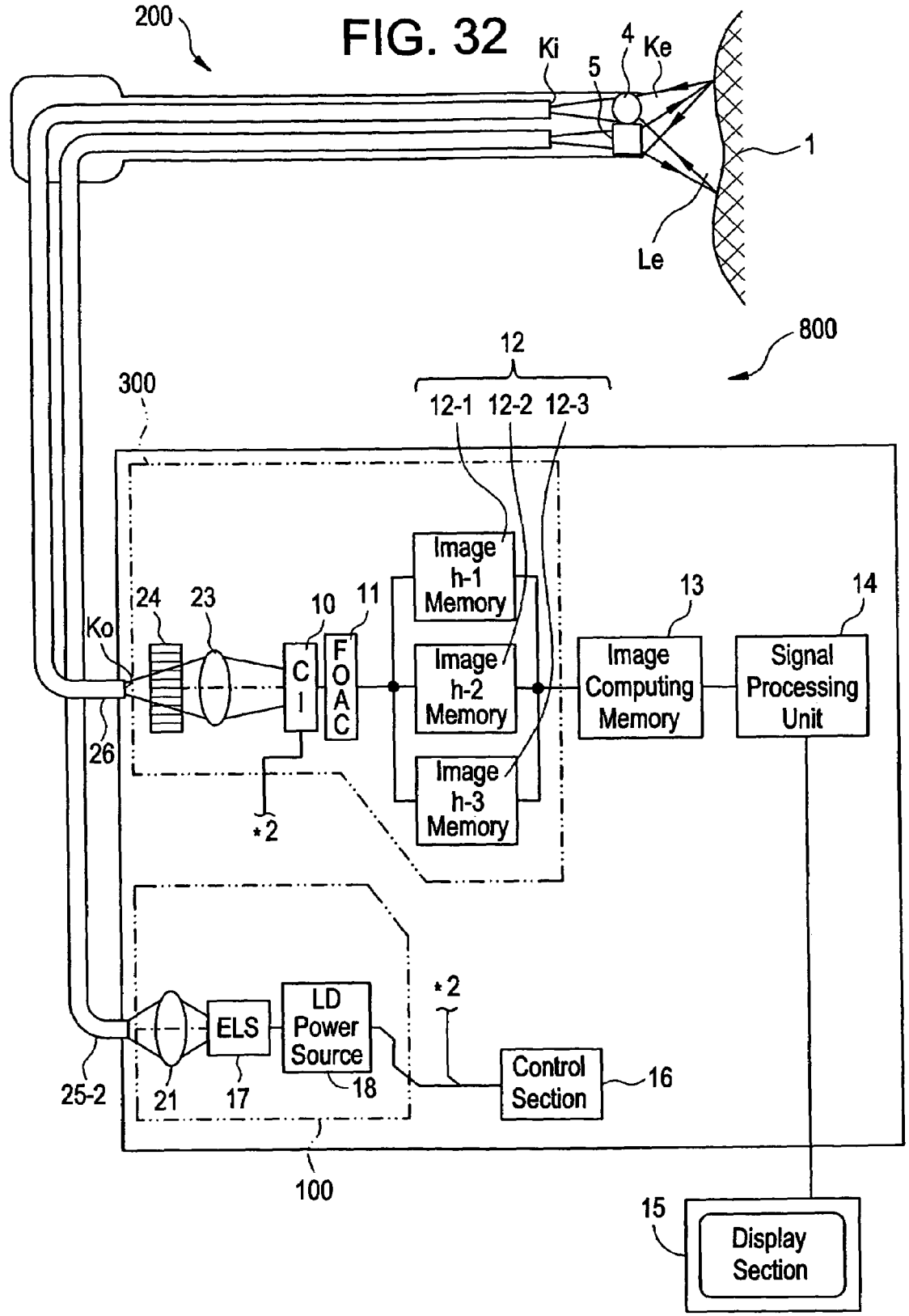
FIG. 32 is a block diagram showing a fluorescence observing apparatus constructed according to a seventh embodiment of the present invention.

FIG. 32 illustrates a seventh embodiment of the fluorescence observing apparatus constructed according to the present invention, parts with a function similar to the first embodiment being shown with the same reference numerals and characters as the first embodiment.

The fluorescence observing apparatus 800 in the seventh embodiment is the same as the first embodiment, except that the components such as the white light source for irradiating white light Wh to the tissue 1, and the components such as the normal observation CCD imager for forming a normal image, are removed.

Next, a description will be given of the operation in the above-mentioned seventh embodiment.

Figure 33:
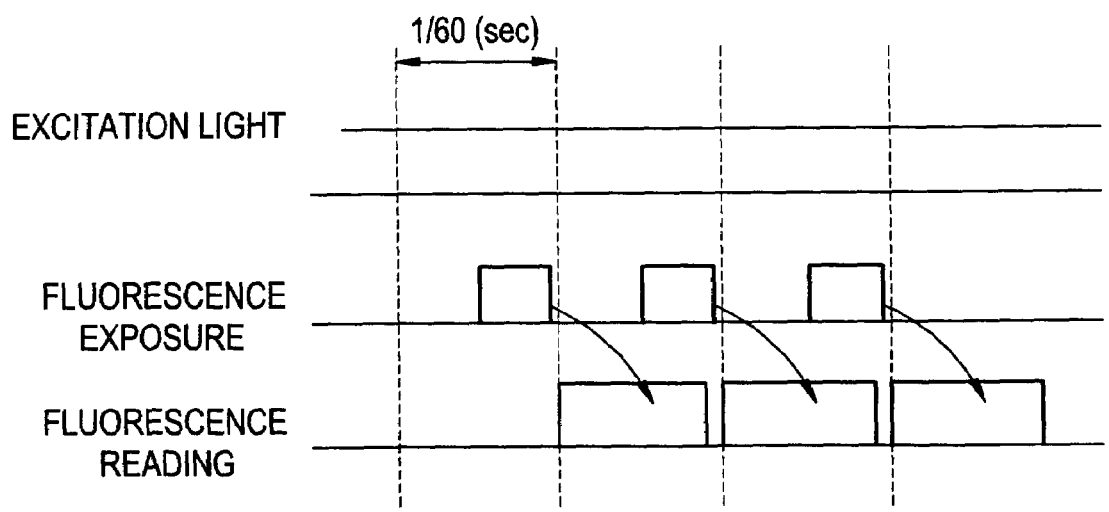
FIG. 33 is a timing chart showing the timing at which excitation light is irradiated.

It has been described in the above-mentioned first through the sixth embodiments that the pulsed excitation light Le is irradiated to the tissue 1. However, in the seventh embodiment, as shown in a timing chart of FIG. 33, continuous excitation light is irradiated to a sample (e.g., a tissue, etc.), by performing CW drive of the semiconductor laser of the excitation light source 17 at all times (i.e., without switching the CW drive on or off) and also without intermittently intercepting the excitation light emitted from the semiconductor laser, as in the above-mentioned sixth embodiment. A fluorescent image alone is formed and displayed. The remaining operation in the seventh embodiment is the same as the first embodiment.

While it has been described in each of the aforementioned first through the seventh embodiments that the active layer employs the InGaN semiconductor laser of InGaN/InGaN multi-quantum cell structure as the excitation light source, the same effect can be obtained even if other InGaN-based semiconductors laser or GaN-based semiconductor lasers are employed.

Also, GaN broad area type or GaN surface emission type semiconductor lasers may be employed as the aforementioned semiconductor laser. An inexpensive and high-output excitation light source can be obtained with these semiconductor lasers. In addition, in the case where a single semiconductor laser gives rise to underoutput, the desired output can be obtained by employing an array type semiconductor laser having a plurality of laser-light emitting points, or by driving a plurality of semiconductor lasers in parallel, as shown in the fifth embodiment.

Moreover, the temperature controlling system described in the aforementioned first embodiment is applicable to each of the aforementioned embodiments, and the same effect as the first embodiment can be obtained.

Furthermore, while it has primarily been described in the aforementioned embodiments that the fluorescence observing apparatus according to the present invention is applied to an endoscope for diagnosing cancerous tissues, the fluorescence observing apparatus according to the present invention can also be applied to operation microscopes, colposcopes, etc., and is applicable for diagnosing morbid tissues other than cancerous tissues.

According to the present invention, as described above, the fluorescence observing apparatus equipped with a light source capable of irradiating high-output excitation light can be reduced in size and cost by optimizing the material of the semiconductor laser, the setting of the drive method, etc.

While the present invention has been described with reference to the preferred embodiments thereof, the invention is not to be limited to the details given herein, but may be modified within the scope of the appended claims.

In addition, all of the contents of the Japanese Patent Application Nos. 11 (1999)-192487 and 2000-114702 are incorporated into this specification by reference.

What is claimed is:

1. A fluorescence observing apparatus comprising: a light source for emitting excitation light; excitation light irradiation means for irradiating said excitation light to a sample; and fluorescence measurement means for measuring fluorescence emitted from said sample by the irradiation of said excitation light, wherein a GaN-based semiconductor laser is employed as said light source, wherein an active layer of said semiconductor laser has InGaN/InGaN quantum cell structure.

2. The fluorescence observing apparatus as set forth in claim 1, wherein said semiconductor laser is caused to output pulsed excitation light having a peak value greater than or equal to a continuous maximum output value of said semiconductor laser by a pulse-injecting current.

3. The fluorescence observing apparatus as set forth in claim 1, wherein said semiconductor laser is an array type semiconductor laser.

4. The fluorescence observing apparatus as set forth in claim 1, wherein said semiconductor laser is a surface emission type semiconductor laser.

5. The fluorescence observing apparatus as set forth in claim 1, wherein said semiconductor laser is a broad area type semiconductor laser.

6. The fluorescence observing apparatus as set forth in claim 1, further comprising visible-light irradiation means for intermittently irradiating visible light to said sample; and normal image forming means for forming a normal image of said sample illuminated with said visible light, wherein said pulsed excitation light is irradiated during a non-irradiation period of said visible light.

7. The fluorescence observing apparatus as set forth in claim 1, wherein a pulsed excitation light is formed from a plurality of pulses.

8. A fluorescence observing apparatus comprising: a light source for emitting excitation light; excitation light irradiation means for irradiating said excitation light to a sample; and fluorescence measurement means for measuring fluorescence emitted from said sample by the irradiation of said excitation light, wherein a GaN-based semiconductor laser is employed as said light source, wherein said semiconductor laser is a broad area type semiconductor laser.

9. The fluorescence observing apparatus as set forth in claim 8, wherein said semiconductor laser is an array type semiconductor laser.

10. The fluorescence observing apparatus as set forth in claim 8, further comprising visible-light irradiation means for intermittently irradiating visible light to said sample; and normal image forming means for forming a normal image of said sample illuminated with said visible light, wherein said pulsed excitation light is irradiated during a non-irradiation period of said visible light.

11. The fluorescence observing apparatus as set forth in claim 8, wherein a pulsed excitation light is formed from a plurality of pulses.

12. A fluorescence observing apparatus comprising: a light source for emitting excitation light; excitation light irradiation means for irradiating said excitation light to a sample; and fluorescence measurement means for measuring fluorescence emitted from said sample by the irradiation of said excitation light, wherein a GaN-based semiconductor laser is employed as said light source, wherein said semiconductor laser is a broad area type semiconductor laser wherein said excitation light emitted from said light source is pulsed excitation light and said excitation light irradiation means irradiates said pulsed excitation light to said sample.

13. A fluorescence observing apparatus comprising: a light source for emitting excitation light; excitation light irradiation means for irradiating said excitation light to a sample; and fluorescence measurement means for measuring fluorescence emitted from said sample by the irradiation of said excitation light, wherein a GaN-based semiconductor laser is employed as said light source, wherein said semiconductor laser is a broad area type semiconductor laser; wherein said GaN-based semiconductor laser is an InGaN-based semiconductor laser.

14. A fluorescence observing apparatus comprising: a light source for emitting excitation light; excitation light irradiation means for irradiating said excitation light to a sample; and fluorescence measurement means for measuring fluorescence emitted from said sample by the irradiation of said excitation light, wherein a GaN-based semiconductor laser is employed as said light source, wherein said semiconductor laser is caused to output pulsed excitation light having a peak value greater than or equal to a continuous maximum output value of said semiconductor laser by a pulse-injecting current, wherein said excitation light emitted from said light source is pulsed excitation light and said excitation light irradiation means irradiates said pulsed excitation light to said sample, and wherein said semiconductor laser is a broad area type semiconductor laser.

15. A fluorescence observing apparatus comprising: a light source for emitting excitation light; excitation light irradiation means for irradiating said excitation light to a sample; and fluorescence measurement means for measuring fluorescence emitted from said sample by the irradiation of said excitation light, wherein a GaN-based semiconductor laser is employed as said light source, wherein said semiconductor laser is caused to output pulsed excitation light having a peak value greater than or equal to a continuous maximum output value of said semiconductor laser by a pulse-injecting current, wherein said excitation light emitted from said light source is pulsed excitation light and said excitation light irradiation means irradiates said pulsed excitation light to said sample, and wherein said semiconductor laser is driven so that an integrated value of pulse oscillation output values of said semiconductor laser per unit time becomes less than or equal to an integrated value of the continuous maximum output values of said semiconductor laser per unit time, and wherein said semiconductor laser is a broad area type semiconductor laser.

16. A fluorescence observing apparatus comprising: a light source for emitting excitation light; excitation light irradiation means for irradiating said excitation light to a sample; and fluorescence measurement means for measuring fluorescence emitted from said sample by the irradiation of said excitation light, wherein a GaN-based semiconductor laser is employed as said light source, wherein said semiconductor laser is a surface emission type semiconductor laser.

17. The fluorescence observing apparatus as set forth in claim 16, wherein said semiconductor laser is an array type semiconductor laser.

18. The fluorescence observing apparatus as set forth in claim 16, further comprising visible-light irradiation means for intermittently irradiating visible light to said sample; and normal image forming means for forming a normal image of said sample illuminated with said visible light, wherein a pulsed excitation light is irradiated during a non-irradiation period of said visible light.

19. The fluorescence observing apparatus as set forth in claim 16, wherein a pulsed excitation light is formed from a plurality of pulses.

20. A fluorescence observing apparatus comprising: a light source for emitting excitation light; excitation light irradiation means for irradiating said excitation light to a sample; and fluorescence measurement means for measuring fluorescence emitted from said sample by the irradiation of said excitation light, wherein a GaN-based semiconductor laser is employed as said light source, wherein said semiconductor laser is a surface emission type semiconductor laser; wherein said excitation light emitted from said light source is pulsed excitation light and said excitation light irradiation means irradiates said pulsed excitation light to said sample.

21. A fluorescence observing apparatus comprising: a light source for emitting excitation light; excitation light irradiation means for irradiating said excitation light to a sample; and fluorescence measurement means for measuring fluorescence emitted from said sample by the irradiation of said excitation light, wherein a GaN-based semiconductor laser is employed as said light source, wherein said semiconductor laser is a surface emission type semiconductor laser; wherein said GaN-based semiconductor laser is an InGaN-based semiconductor laser.

22. A fluorescence observing apparatus comprising: a light source for emitting excitation light; excitation light irradiation means for irradiating said excitation light to a sample; and fluorescence measurement means for measuring fluorescence emitted from said sample by the irradiation of said excitation light, wherein a GaN-based semiconductor laser is employed as said light source, wherein said semiconductor laser is caused to output pulsed excitation light having a peak value greater than or equal to a continuous maximum output value of said semiconductor laser by a pulse-injecting current, wherein said excitation light emitted from said light source is pulsed excitation light and said excitation light irradiation means irradiates said pulsed excitation light to said sample, and wherein said semiconductor laser is a surface emission type semiconductor laser.

23. A fluorescence observing apparatus comprising: a light source for emitting excitation light; excitation light irradiation means for irradiating said excitation light to a sample; and fluorescence measurement means for measuring fluorescence emitted from said sample by the irradiation of said excitation light, wherein a GaN-based semiconductor laser is employed as said light source, wherein said semiconductor laser is caused to output pulsed excitation light having a peak value greater than or equal to a continuous maximum output value of said semiconductor laser by a pulse-injecting current, wherein said excitation light emitted from said light source is pulsed excitation light and said excitation light irradiation means irradiates said pulsed excitation light to said sample, and wherein said semiconductor laser is driven so that an integrated value of pulse oscillation output values of said semiconductor laser per unit time becomes less than or equal to an integrated value of the continuous maximum output values of said semiconductor laser per unit time, and wherein said semiconductor laser is a surface emission type semiconductor laser.

24. A fluorescence observing apparatus comprising: a light source for emitting excitation light; excitation light irradiation means for irradiating said excitation light to a sample; and fluorescence measurement means for measuring fluorescence emitted from said sample by the irradiation of said excitation light, wherein a GaN-based semiconductor laser is employed as said light source, wherein said semiconductor laser is an array type semiconductor laser; wherein said excitation light emitted from said light source is pulsed excitation light and said excitation light irradiation means irradiates said pulsed excitation light to said sample.

25. A fluorescence observing apparatus comprising: a light source for emitting excitation light; excitation light irradiation means for irradiating said excitation light to a sample; and fluorescence measurement means for measuring fluorescence emitted from said sample by the irradiation of said excitation light, wherein a GaN-based semiconductor laser is employed as said light source, wherein said semiconductor laser is an array type semiconductor laser; wherein said GaN-based semiconductor laser is an InGaN-based semiconductor laser.

26. A fluorescence observing apparatus comprising: a light source for emitting excitation light; excitation light irradiation means for irradiating said excitation light to a sample; and fluorescence measurement means for measuring fluorescence emitted from said sample by the irradiation of said excitation light, wherein a GaN-based semiconductor laser is employed as said light source, wherein said semiconductor laser is caused to output pulsed excitation light having a peak value greater than or equal to a continuous maximum output value of said semiconductor laser by a pulse-injecting current, wherein said excitation light emitted from said light source is pulsed excitation light and said excitation light irradiation means irradiates said pulsed excitation light to said sample, and wherein said semiconductor laser is an array type semiconductor laser.

27. A fluorescence observing apparatus comprising: a light source for emitting excitation light; excitation light irradiation means for irradiating said excitation light to a sample; and fluorescence measurement means for measuring fluorescence emitted from said sample by the irradiation of said excitation light, wherein a GaN-based semiconductor laser is employed as said light source, wherein said semiconductor laser is caused to output pulsed excitation light having a peak value greater than or equal to a continuous maximum output value of said semiconductor laser by a pulse-injecting current, wherein said excitation light emitted from said light source is pulsed excitation light and said excitation light irradiation means irradiates said pulsed excitation light to said sample, and wherein said semiconductor laser is driven so that an integrated value of pulse oscillation output values of said semiconductor laser per unit time becomes less than or equal to an integrated value of the continuous maximum output values of said semiconductor laser per unit time, and wherein said semiconductor laser is an array type semiconductor laser.

* * * * *